(12) United States Patent
Nakatani et al.

(10) Patent No.: US 7,306,564 B2
(45) Date of Patent: Dec. 11, 2007

(54) BREATH MONITOR

(75) Inventors: Hiroto Nakatani, Nagoya (JP);
Noriyuki Ozaki, Kariya (JP); Kenichi Yanai, Nisshin (JP)

(73) Assignee: DENSO CORPORATION, Kariya (JP)

( * ) Notice: Subject to any disclaimer, the term of this patent is extended or adjusted under 35 U.S.C. 154(b) by 533 days.

(21) Appl. No.: 10/950,424

(22) Filed: Sep. 28, 2004

(65) Prior Publication Data

US 2005/0113711 A1    May 26, 2005

(30) Foreign Application Priority Data

Nov. 26, 2003  (JP)  ............................. 2003-395598
Jan. 14, 2004  (JP)  ............................. 2004-007237

(51) Int. Cl.
*A61B 5/08*  (2006.01)

(52) U.S. Cl. .................. 600/534; 600/529; 600/535

(58) Field of Classification Search ................ 600/535
See application file for complete search history.

(56) References Cited

U.S. PATENT DOCUMENTS

| 5,086,777 | A * | 2/1992 | Hishii ........................ 600/578 |
| 6,280,392 | B1 * | 8/2001 | Yoshimi et al. ............. 600/534 |
| 6,450,957 | B1 * | 9/2002 | Yoshimi et al. ............. 600/309 |
| 2003/0167019 | A1 * | 9/2003 | Viertio-Oja et al. ........ 600/544 |
| 2004/0010202 | A1 * | 1/2004 | Nakatani et al. ............ 600/529 |

* cited by examiner

*Primary Examiner*—Max F. Hindenburg
*Assistant Examiner*—Patricia C Mallari
(74) *Attorney, Agent, or Firm*—Posz Law Group, PLC

(57) ABSTRACT

A breath monitor includes: a plurality of sensors for detecting a load derived from a human lying on a bed and for outputting a sensor signal corresponding to the load; and breath signal computation means. The sensors are disposed under the human with a predetermined arrangement. The breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors.

40 Claims, 11 Drawing Sheets

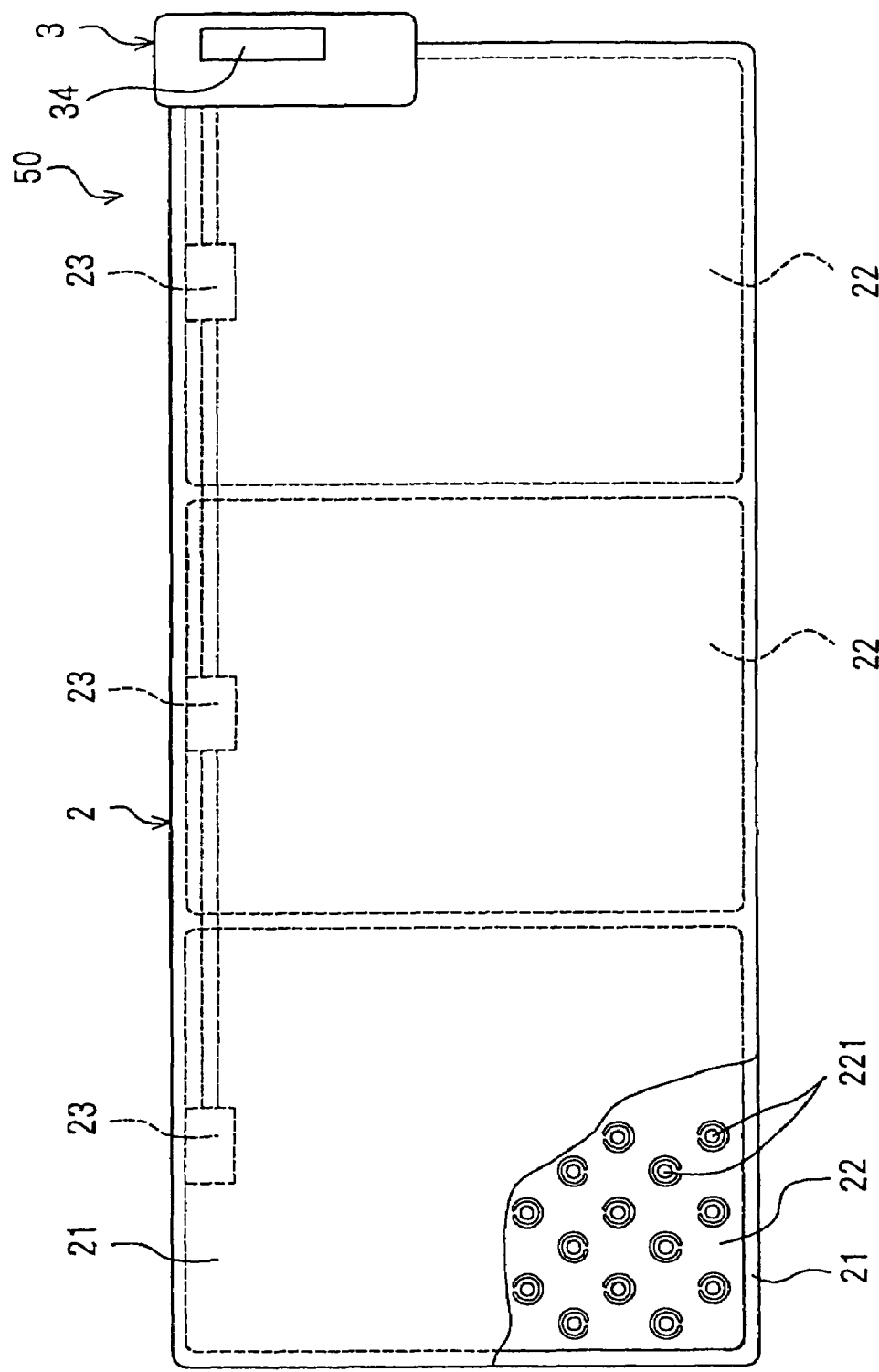

BREATH MONITOR

CROSS REFERENCE TO RELATED APPLICATIONS

This application is based on Japanese Patent Applications No. 2003-395598 filed on Nov. 26, 2003, and No. 2004-7237 filed on Jan. 14, 2004, the disclosures of which are incorporated herein by reference.

FIELD OF THE INVENTION

The present invention relates to a breath monitor for monitoring breath of a human.

BACKGROUND OF THE INVENTION

A breath monitor for monitoring breath of a human while sleeping is disclosed in Japanese Patent Application Publication No. 2001-37742, which corresponds to U.S. Pat. No. 6,450,957. Specifically, the monitor is suitably used for diagnosing a patient having a respiratory disease. A sensor of the monitor is disposed under bedclothes to have a predetermined arrangement. The monitor includes multiple loading sensors for detecting an applied load of the patient. Each sensor outputs a load signal (i.e., a weight signal) as a sensor signal in accordance with the applied load. A breath signal is calculated from the weight signals such that a part of the weight signals having a certain frequency corresponding to a breathing rate of the patient is selected.

The monitor calculates the breath signal in detail as follows. Firstly, the weight signals outputted from the loading sensor are processed by a frequency analysis so that a power spectrum having a frequency range corresponding to the breathing rate is calculated. Then, one of the loading sensors, which has the maximum strength (i.e., maximum intensity) of the power spectrum, is selected as the first reference sensor. Another one of the sensors, which outputs the weight signal having the same phase or the reverse phase of the first reference sensor, is selected as the second reference sensor. When the second reference sensor outputs the weight signal having the same phase of the first reference sensor, the weight signals of the first and second reference sensors are added. When the second reference sensor outputs the weight signal having the reverse phase of the first reference sensor, the weight signal of the second reference sensor is reversed so that the weight signals of the first and second reference sensors are added. Thus, the breath signal is obtained by adding the weight signals.

However, the loading sensor may detect other loads caused by, for example, a motion of the patient instead of the load caused by the breathing. When the motion of the patient is larger than the breathing, the load by the motion is larger than that by the breathing. When the load by the motion is applied to one of the sensors, the one of the sensors may be selected as the first reference sensor. In this case, the monitor cannot detect the breath signal accurately.

Further, the breath monitor is suitably used for detecting apnea symptom of the patient so that a person such as a doctor or a nurse as an operator of the monitor diagnoses apnea syndrome of the patient while sleeping. It is required for the breath monitor to detect apnea symptom and/or hypopnea of the patient. However, the monitor according to the prior art cannot detect the hypopnea of the patient with high accuracy.

SUMMARY OF THE INVENTION

In view of the above-described problem, it is an object of the present invention to provide a breath monitor for monitoring breath of a human accurately. It is another object of the present invention to provide detection equipment for detecting apnea symptom and hypopnea of a human.

A breath monitor includes: a plurality of sensors for detecting a load derived from a human lying on a bed and for outputting a sensor signal corresponding to the load; and breath signal computation means. The sensors are disposed under the human with a predetermined arrangement. The breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors.

In this case, the sensor outputting the sensor signal corresponding to the breath of the human can be selected appropriately so that the breath signal is obtained with high accuracy. Therefore, the accuracy of the breath signal is improved. Thus, the breath monitor monitors breath of a human accurately.

Preferably, the spectrum is a power spectrum having a relationship between an intensity and a frequency of the sensor signal. Preferably, the breath signal computation means selects the sensors in such a manner that a peak frequency in the spectrum of each sensor signal is determined, a maximum frequency range having a predetermined frequency width, in which the largest number of peak frequencies of the sensor signals are disposed, is determined, and the sensor signals having the peak frequency disposed in the maximum frequency range are selected. More preferably, the breath signal computation means computes the breath signal in such a manner that the sensor signals outputted from the selected sensors are classified into a plurality of phase groups having a predetermined phase width on the basis of a phase of the sensor signal, a maximum phase group having the largest number of classified sensor signals is determined, an opposite phase group having the phase shifted by a half period from a center phase of the maximum phase group is determined, all phases of the sensor signals disposed in one of the maximum phase group and the opposite phase group are inverted, and the inverted sensor signals in the one of the phase groups are added to the sensor signals in the other one of the phase groups so that the breath signal is obtained.

Preferably, the breath monitor further includes determination means for determining a quick movement of the human. The breath signal includes a plurality of cycles, the number of which is predetermined, and each of which corresponds to one cycle of breathing of the human. The determination means arbitrarily selects one cycle of the breath signal, compares an amplitude of the one cycle of the breath signal to an amplitude of another cycle of the breath signal, and determines the quick movement when the amplitude of the one cycle is larger by a predetermined reference value than the amplitude of the other cycle. Preferably, the breath monitor further includes determination means for determining a slight movement of the human. The breath signal computation means converts the sensor signals, each of which has a signal intensity larger than a predetermined value so that the sensor signal only derived from the load of the human is selected. The determination means determines the number of the sensor signals having the signal intensity larger than the predetermined value. The determination means determines the slight movement when the number of the sensor signals changes by a predetermined number as time advances.

Further, detection equipment for detecting an apnea syndrome includes: breath signal computation means for computing a breath signal on the basis of a change of a load, which corresponds to a body movement of breathing of a person; and determination means for determining an apnea symptom and a hypopnea symptom of the person on the basis of a periodicity of extremums of an amplitude envelope curve of the breath signal.

In this case, since the apnea symptom and the hypopnea symptom are determined on the basis of the periodicity of the extremums, the threshold can be much reduced when the extremums are determined. Accordingly, the detection equipment can detect a slight apnea symptom.

Preferably, the amplitude envelope curve includes a plurality of pairs of a maximum value and a minimum value, a pair of which is temporally adjacent each other, and defined as MAX(k) and MIN(k) (k=0, 1, 2, ..., N), respectively. The maximum value of MAX(k) is occurred at a time defined as TMAX(k) (k=0, 1, 2, ..., N). The minimum value of MIN(k) is occurred at a time defined as TMIN(k) (k=0, 1, 2, ..., N). The maximum value of MAX(k) and the temporally adjacent maximum value of MAX(k−1) provide a time interval defined as TIMAX(k)=TMAX(k)−TMAX(k−1). The minimum value of MIN(k) and the temporally adjacent minimum value of MIN(k−1) provide a time interval defined as TIMIN(k)=TMIN(k)−TMIN(k−1). The determination means determines the apnea symptom and the hypopnea symptom occurred at the time of TMIN(k) in a case where the time intervals of TIMIN(k) and TIMAX(k) satisfy a condition of: TIMIN(k)<C1; TIMAX(k)<C2; TIMIN(k−1)<C1; and TIMAX(k−1)<C2. Here, C1 and C2 are predetermined constant values. More preferably, the time intervals of TIMIN(k) of the minimum values of MIN(k) have an average time interval defined as $$AVMIN = \sum_{k=1}^{N} TIMIN(k)/N.$$

The time intervals of TIMAX(k) of the maximum values of MAX(k) have an average time interval defined as $$AVMAX = \sum_{k=1}^{N} TIMAX(k)/N.$$

The predetermined constant values of C1 and C2 are defined as: C1=AVMIN+α; and C2=AVMAX+α. Here, a is a predetermined constant value.

Preferably, the amplitude envelope curve includes a plurality of pairs of a maximum value and a minimum value, a pair of which is temporally adjacent each other, and defined as MAX(k) and MIN(k) (k=0, 1, 2, ..., N), respectively. The maximum value of MAX(k) is occurred at a time defined as TMAX(k) (k=0, 1, 2, ..., N). The minimum value of MIN(k) is occurred at a time defined as TMIN(k) (k=0, 1, 2, ..., N). The maximum value of MAX(k) and the temporally adjacent maximum value of MAX(k−1) provide a time interval defined as TIMAX(k)=TMAX(k)−TMAX(k−1). The minimum value of MIN(k) and the temporally adjacent minimum value of MIN(k−1) provide a time interval defined as TIMIN(k)=TMIN(k)−TMIN(k−1). The determination means determines the apnea symptom and the hypopnea symptom occurred at the time of TMIN(k) in a case where the time intervals of TIMIN(k) and TIMAX(k) satisfy a condition of: C3<TIMIN(k)<C1; C4<TIMAX(k)<C2; C3<TIMIN(k−1)<C1; and C4<TIMAX(k−1)<C2. Here, C1, C2, C3 and C4 are predetermined constant values. More preferably, the time intervals of TIMIN(k) of the minimum values of MIN(k) has an average time interval defined as $$AVMIN = \sum_{k=1}^{N} TIMIN(k)/N.$$

The time intervals of TIMAX(k) of the maximum values of MAX(k) has an average time interval defined as $$AVMAX = \sum_{k=1}^{N} TIMAX(k)/N.$$

The predetermined constant values of C1, C2, C3 and C4 are defined as: C1=AVMIN+α; C2=AVMAX+α; C3=AVMIN−β; and C4=AVMAX−β. Here, α and β are predetermined constant values.

Preferably, the breath signal includes a plurality of cycles, the number of which is predetermined, and each of which corresponds to one cycle of breathing of the person and has an amplitude. The amplitude envelope curve is obtained in such a manner that all amplitudes of cycles in the breath signal are interpolated so that the amplitude envelope curve is computed.

BRIEF DESCRIPTION OF THE DRAWINGS

The above and other objects, features and advantages of the present invention will become more apparent from the following detailed description made with reference to the accompanying drawings. In the drawings:

FIG. 2 is a plan view showing the monitor according to the first embodiment;

DETAILED DESCRIPTION OF THE PREFERRED EMBODIMENTS

First Embodiment

Figure 1:
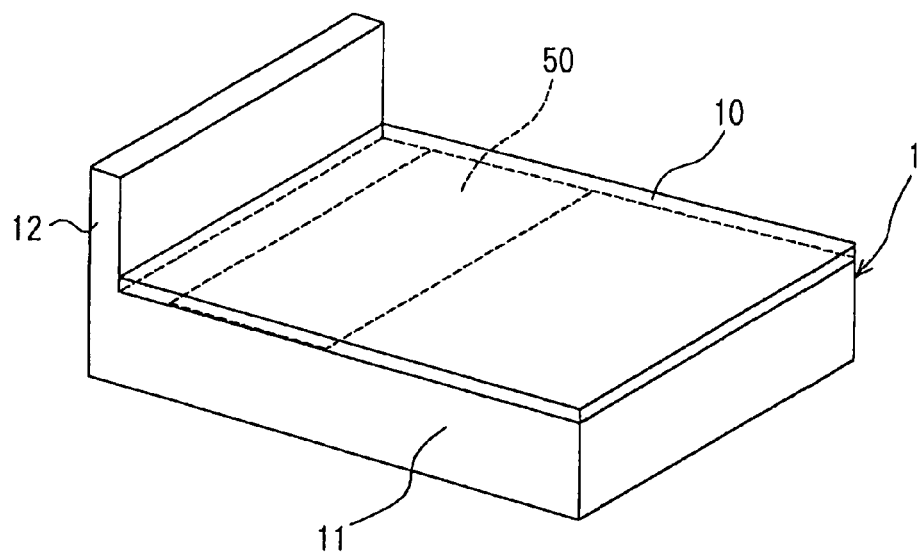
FIG. 1 is a perspective view showing an arrangement of a breath monitor according to a first embodiment of the present invention.

A breath monitor according to a first embodiment of the present invention includes a plurality of sensors for detecting a load or a vibration derived from a human, i.e., a patient lying on a bed and for outputting a sensor signal corresponding to the load or the vibration; and breath signal computation means. For example, the sensor is a pressure sensor so that the sensor detects the load derived from a weight of the human. Or, the sensor is a vibration sensor so that the sensor detects the load derived form a vibration of a body movement of the human. The sensors are disposed under the human with a predetermined arrangement. The breath signal computation means converts the sensor signal to a frequency domain, selects the sensor on the basis of the converted sensor signal, and computes the breath signal on the basis of the sensor signal outputted from the selected sensor. Here, the sensor is arranged with the predetermined arrangement. The predetermined arrangement is, for example, an equally-spaced distribution or an uneven space distribution corresponding to a breath motion of the patient.

The inventors focus on the fact that the motion of the patient corresponding to the breath can be confirmed at many portions of a body of the patient. In the above breath monitor having multiple sensors, the sensor signal of the sensor has various characteristics corresponding to the motion of the patient. The sensor detects the motion of the body derived from not only the breath but also a quick movement of the body or a slight movement of the body. For example, the characteristics of the sensor signal are periodicity or correlation of a waveform. Therefore, to detect these characteristics easily, the sensor signal, i.e., the output signal is converted into a frequency domain, i.e., a frequency range so that the monitor detects the breath with high accuracy by selecting the sensor having a predetermined characteristic of the converted output signal.

Thus, the breath signal is computed from the sensor signal outputted from the selected sensor so that almost all of the sensor signals outputted from the sensor corresponding to the motion except for the breath are removed. Accordingly, the accuracy of detecting the breath signal is improved.

Here, preferably, the breath signal computation means determines a peak frequency in a spectrum of the sensor signal outputted from the sensor, determines a maximum frequency range, in which most peak frequencies are disposed, selects the sensor outputting the sensor signal having the peak frequency disposed in the maximum frequency range, and computes the breath signal on the basis of the sensor signal outputted from the selected sensor. Here, the peak frequency is, for example, a frequency having maximum amplitude in a case where the sensor signal is converted into an amplitude spectrum or a frequency having maximum power in a case where the sensor signal is converted into the power spectrum. Further, the peak frequency can be defined as the frequency having the second or third largest amplitude or power. Preferably, the maximum frequency range has, for example, a frequency width of 0.03 Hz.

The inventors further focus on the facts that the number of the sensors outputting the sensor signal having the peak frequency corresponding to the breath of the patient is larger than the number of the sensors outputting the sensor signal having the peak frequency corresponding to the other motion such as the slight movement or the quick movement of the body of the patient. For example, when the patient moves his right arm, the sensor disposed under the right arm outputs the sensor signal having the peak frequency corresponding to the motion of the right arm. However, the sensor disposed under the shoulder, the waist or the back of the patient can output the sensor signal having the peak frequency corresponding to the breath of the patient even when the patient moves his right arm.

Accordingly, when the maximum frequency range including most peak frequencies is selected, the sensor signal corresponding to the breath has the peak frequency disposed in the maximum frequency range. Therefore, the sensor outputting the sensor signal having the peak frequency disposed in the determined frequency range (i.e., the maximum frequency range) can be selected. The breath signal is computed on the basis of the sensor signal outputted from the selected sensor. In this case, the sensor signal corresponding to the other motion of the breath is removed so that the breath signal is computed precisely. Thus, the accuracy of the breath signal is improved.

Here, the breath signal computation means can determine the maximum frequency range by using only a criterion that the maximum frequency range includes most peak frequencies without any condition. However, in this case, when the patient moves his body widely, for example, when the patient turns over on the bed, the breath signal computation means may select the maximum frequency range corresponding to the turn over of the patient. Therefore, it is preferred that the breath signal computation means determines the maximum frequency range by using only the peak frequency disposed in a predetermined breath frequency range. Here, the predetermined breath frequency range is, for example, in a range between 0.2 Hz and 0.5 Hz. In this case, even when the patient turns over on the bed and many sensors detect the motion of the turn-over, the sensor signal derived from the turn-over is removed in a case where the maximum frequency range is determined to be in a range between 0.2 Hz and 0.5 Hz. Thus, the accuracy of the breath signal is improved.

Further, the breath signal computation means can compute the breath signal such that all sensor signals outputted from the selected sensors are added and averaged. However, in this case, important or useful information included in the sensor signal may be disappeared by averaging. Because the motion according to the breath has various phase of waveform. For example, a part of the back of the patient disposed near the shoulder has the motion corresponding to the breath, the motion having a certain phase of the waveform. Another part of the back disposed near the waist has another motion corresponding to the breath, the motion having another certain phase of the waveform, which is different by a half period from the phase derived from the part near the shoulder. Therefore, when the sensor signal having the certain phase is added to another sensor signal having the phase shifted by half period from the certain phase, the sensor signals may be canceled. Further, at the other portions of the body, the sensor signals have different phase shifts, respectively.

Accordingly, it is preferred that the breath signal computation means computes the breath signal in such a manner that the breath signal computation means classifies the sensor signal outputted from the selected sensor into a phase group having a predetermined phase width on the basis of a phase of the sensor signal, selects maximum phase group having most sensor signals, selects another phase group having a phase shifted by a half period from a center phase of the maximum phase group, inverts the phase of the sensor signal in one of the phase groups, and adds the inverted sensor signal in the one of the phase groups to the sensor signal in the other one of the phase groups so that the breath signal is computed. Here, the sensor signal is classified into the phase group on the basis of the phase of the sensor signal, and the phase group is provided such that $2\pi$ as one period is, for example, divided equally into ten phase groups so that each phase group has the phase width of $\pi/5$. In this case, the center phase of the phase group having the phase width in a range between 0 and $\pi/5$ is $\pi/10$.

When the breath signal is computed, the phase of the sensor signal classified in one of the phase groups is inverted so that the amplitude of the sensor signal is inverted, and the inverted sensor signal is added to the sensor signal classified in the other one of the phase groups so that the breath signal is computed. In this case, the sensor signals are not canceled. Further, the phase of the sensor signal classified in the one of the phase groups can be shifted by a half period of $\pi$ in a direction, in which the difference of the center phase between the one and the other one of the phase groups becomes smaller, and the shifted sensor signal can be added to the sensor signal classified in the other one of the phase groups so that the breath signal is computed. Furthermore, after the two sensor signals are added, the added sensor signals can be divided by the number of the sensor signals so that the breath signal is computed.

Thus, since the sensor signals obtained from different parts of the body have different phases, a part of the sensor signals is selected and substantially compensated by reversing the phase of the sensor signals so that the breath signal is computed. Therefore, the breath signal is much precisely computed.

It is considered that information from a motion of a limb of the patient having a certain period may be involved in the sensor signal. To distinguish the information from the motion having the certain periodicity, the breath monitor further includes determination means. The determination means selects one part of the breath signal, which corresponds to one cycle (i.e., one wave length) of the breath signal. The determination means compares the amplitude of the one part of the breath signal to another amplitude of another one part of the breath signal, which corresponds to the one wavelength, so that the motion of the limb having the certain periodicity is determined. Specifically, the determination means determines whether the amplitude of the one part of the breath signal is larger by a predetermined reference value than the other amplitudes. Here, the predetermined reference value is, for example, an absolute value such as 3 volts or a relative value such as twice larger value.

Thus, the determination means determines whether the information is obtained from the motion of the limb of the patient having the certain periodicity. Then, the determination means outputs a determination result to the other device or the determination means informs the determination result to the operator so that the operator monitoring the breath signal knows whether the breath signal includes the information from the motion of the limb except for the breath. The operator is, for example, a doctor, a nurse or an engineer. Thus, the operator can understand the breath signal precisely so that the operator diagnoses a disease such as apnea syndrome.

Further, the breath monitor can be composed of: a plurality of sensors for detecting a load or a vibration derived from a human lying on a bed and for outputting a sensor signal corresponding to the load or the vibration; breath signal computation means; and determination means. The determination means selects the sensor outputting the sensor signal equal to or larger than a predetermined threshold. The determination means determines whether the number of the selected sensors is changed by a predetermined number after a predetermined time passes. In this case, the breath monitor can detect a slight movement of the body, which moves a little in such a manner that the patient shifts his body slightly on the bed. The determination means outputs a determination result to the other device or the determination means informs the determination result to the operator so that the operator monitoring the breath signal knows the information about the slight movement of the body. Thus, when the sensor signal is derived from the slight movement of the body and the determination result is changed, the operator can eliminate the information of the sensor signal from the diagnosis of a disease such as apnea syndrome.

Furthermore, the breath monitor can be composed of: a plurality of sensors for detecting a load or a vibration derived from a human lying on a bed and for outputting a sensor signal corresponding to the load or the vibration; breath signal computation means; and determination means. The determination means determines a peak frequency in a spectrum of the sensor signal outputted from the sensor, and determines the sensor disposed under the human in a case where the peak frequency of the sensor is disposed in a breath frequency range. In this case, the determination means can distinguish the sensor, on which an object is disposed, so that the sensor signal of the sensor corresponding to the object except the body of the patient is eliminated from the breath signal. Thus, the breath signal is computed by using only the sensor signal from the sensor disposed under the body of the patient. Therefore, the breath signal is precisely computed so that the operator can understand the breath of the patient.

In general, the sensor of the breath monitor for detecting the load or the vibration of the patient is required to detect a slight change of the load or the vibration with high accuracy. However, it is considered that an output from electric resistance corresponding to a pressure applied to each sensor may vary widely because of difference of each sensor characteristic. For example, a pressure sensor having a membrane construction is suitably used for the breath monitor. This membrane sensor has a narrow pressure detection range, which is, for example, 1 KPa to 3 KPa. However, preferably, the pressure sensor is required to have the detection range between 1 KPa and 10 KPa and to detect a slight pressure change such as 0.05 KPa to 0.6 KPa. To satisfy both requirements, it is preferred that the breath monitor is composed of: a plurality of sensors for detecting a load or a vibration derived from a human lying on a bed and for outputting a sensor signal corresponding to the load or the vibration; breath signal computation means; and a resistance branch circuit having a sensitivity resistor. Each sensor includes the resistance branch circuit. In this case, the sensor can detect the load or the vibration of the patient and detect the slight change of the load or the vibration with high accuracy. Specifically, the sensor satisfies both requirements. Further, preferably, the breath monitor is composed of: a plurality of sensors for detecting a load or a vibration derived from a human lying on a bed and for outputting a sensor signal corresponding to the load or the vibration; breath signal computation means; a resistance branch circuit having a sensitivity resistor; and a switch for switching a connection between the resistance branch circuit and the sensor. In the above cases, a relationship between the pressure and a detection voltage in the sensor can become linearly, although a relationship between the pressure and the resistance in the sensor is not linear. Therefore, the sensor can detect the sight pressure change with high accuracy.

Next, a breath monitor is described in detail as follows.

A breath monitor 50 according to the first embodiment of the present invention is shown in FIG. 1. FIG. 1 explains a mounting position of the monitor 50 in a bed 1. The bed 1 includes a frame 11 and a backboard 12. The frame 11 supports bedclothes 10 such as a bed pad or a bottom mattress. The backboard 12 is disposed at one end of the frame in a standing manner. The monitor 50 is disposed between the bedclothes 10 and the frame 11 so that the monitor 50 is disposed under the bedclothes 10. Specifically, the monitor 50 is disposed on a backboard side from the center of the frame 11 so that the monitor 50 is disposed in a range between a chest and an abdomen of the patient when the patient lies down on the bed 1.

As shown in FIG. 2, the monitor 50 includes a sheet 2 and a controller 3. The sheet 2 includes a pair of protection sheets 21 and a sensor sheet 22. The sensor sheet 22 is sandwiched between the protection sheets 21. In this embodiment, the sheet 2 includes three sensor sheets 22. Each sensor sheet 22 includes a sensor selector 23. The sensor selector 23 is also sandwiched between the protection sheets 21. The sensor sheet 22 further includes multiple sensors 221. The sensors 221 are disposed at a predetermined interval on the sensor sheet 22. In FIG. 2, the three sensor sheets 22 totally include one hundred and sixty-two sensors 221. Each sensor 221 has a pressure detection device (i.e., a pressure sensitive device) disposed at an electrode of a membrane switch for detecting a load such that electric resistance of the device is changed or reduced in accordance with the applied load. A wiring (not shown) electrically connects between the sensors 221 and the sensor selector 23. The sensor 221 can include a vibration detection device for detecting vibration of the patient. Further, the pressure detection device can be other pressure detection device.

The sensor selector 23 electrically switches connections of the sensors 221 so that a voltage signal outputted from one of the sensors 221 is selectively sent to the controller 3. Thus, when a circuit including the sensors 221 is applied with a predetermined voltage, the electric resistance of the sensor 221 is changed in accordance with the applied load. Thus, the voltage drop in the sensor 221 is changed (i.e., increased or decreased). The controller 3 individually and independently detects the voltage drop of each sensor 221 so that the applied load is detected on the basis of the voltage drop.

Figure 3:
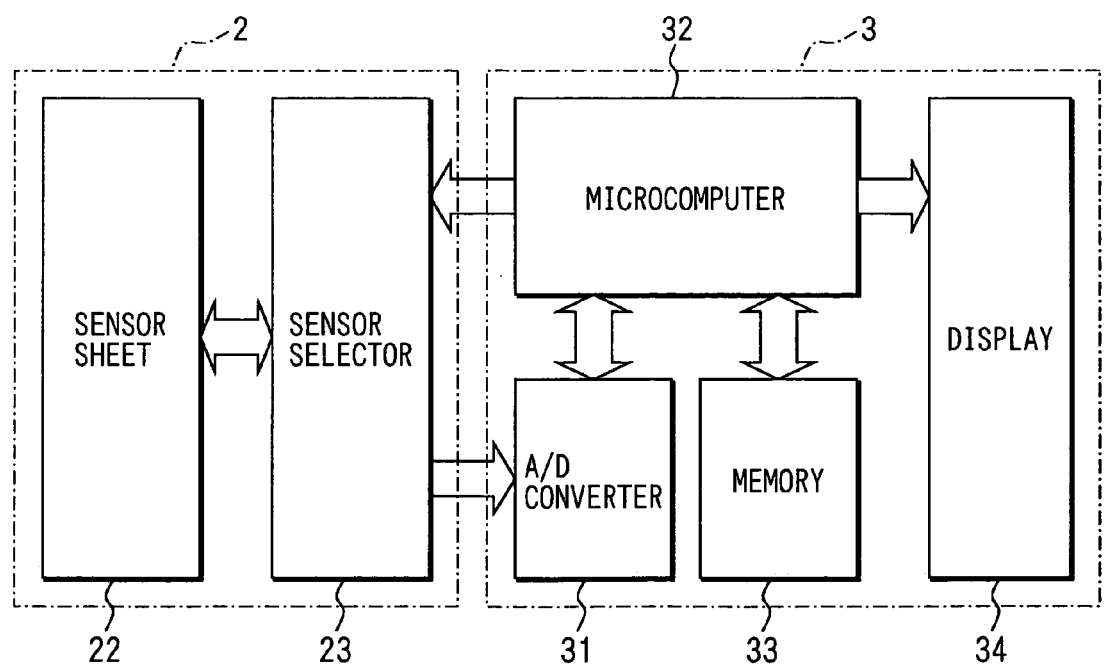
FIG. 3 is a block diagram explaining a controller of the monitor according to the first embodiment.

As shown in FIG. 3, the controller 3 includes an A/D (i.e., analog-digital) converter 31, a microcomputer 32, a memory 33 and a display 34. The A/D converter 31 converts an analog signal to a digital signal. The microcomputer 32 performs various processing. The microcomputer 32 controls the sensor selector 23 such that the microcomputer 32 sends a control signal to the sensor selector 23 and inputs a weight signal i.e., a loading signal as a sensor signal from the sensor sheet 22, i.e., the sensor 221 through the sensor selector 23 and the A/D converter 31. Then, the microcomputer 32 calculates the breath signal on the basis of the weight signal outputted from the sensor 221. Further, the microcomputer 32 processes the breath signal in a breath signal computation process. After that, the microcomputer 32 outputs the processed breath signal to the display 34. This breath signal computation process is described in detail later. The memory 33 memorizes several data. The display 34 is composed of LED (i.e., light emitting diode), a liquid crystal display or the like.

Figure 4:
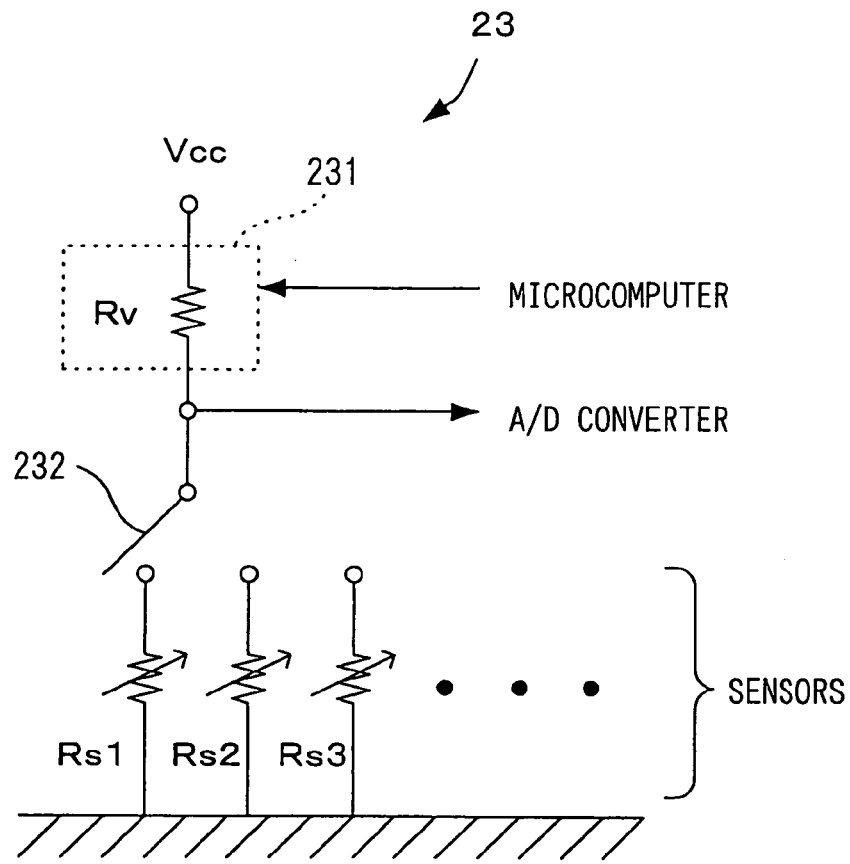
FIG. 4 is a circuit diagram explaining a sensor selector of the monitor according to the first embodiment.

As shown in FIG. 4, the sensor selector 23 includes a digital potentiometer 231 and a switch 232. The digital potentiometer 231 changes a sensitivity resistance Rv according to the control signal from the microcomputer 32. Here, the microcomputer 32 preliminarily resistors the data of the control signal corresponding to each sensor 221. Further, the switch 231 switches an electrical connection between the sensor 221 and the A/D converter 31. The digital potentiometer 231 works as a resistance distribution means and a sensitivity resistance changing means. The switch 232 works as a switching means.

Figure 5:
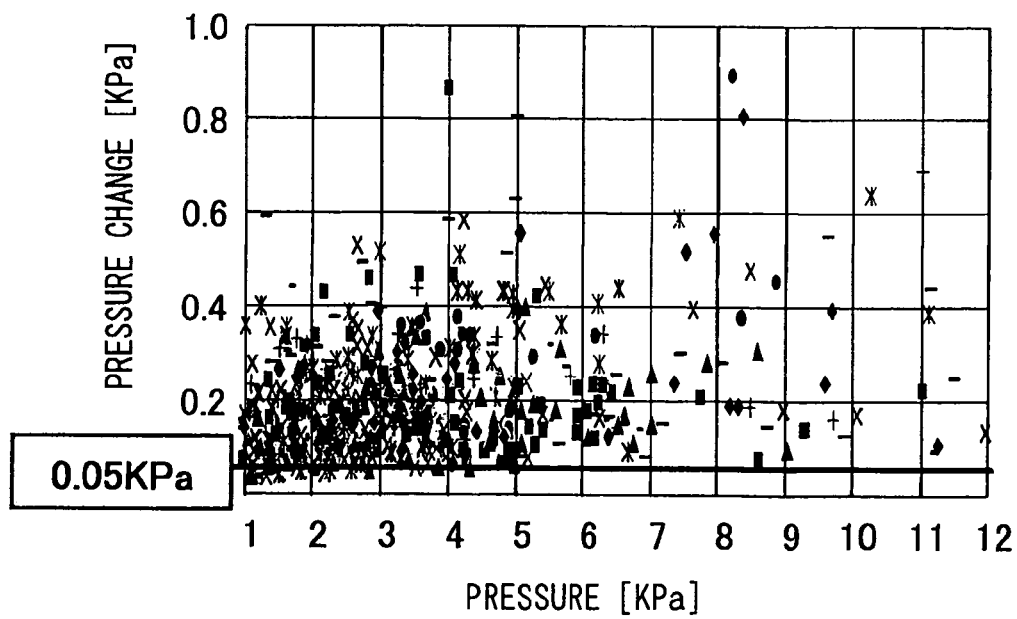
FIG. 5 is a graph showing a relationship between a pressure and a pressure change, according to the first embodiment.

Each sensor 221 has an individual sensor resistance Rs1, Rs2, Rs3, . . . . Assuming that the sensor 221 has a resistance of Rs, the sensitivity resistance Rv is determined as follows. Firstly, the requirement of the detection performance of the sensor 221 is studied. The inventors have studied about a relationship between a pressure from the patient and a pressure change according to the breath of the patient. Specifically, the pressure is provided at each position of the body of the patient. Mainly, the pressure is provided from the back of the patient. At that time, the pressure change according to the breath of the patient is obtained. The results are shown in FIG. 5. In FIG. 5, the relationship between the pressure and the pressure change is obtained from twenty-three persons as a patient including four children. They are men and women, their body heights are in a range between 100 cm and 180 cm, and their body weights are in a range between 15.8 kg and 125 kg. As shown in FIG. 5, when the pressure is disposed in a range between 1 KPa and 2.5 Kpa, it is required to detect the pressure change of at least 0.05 KPa so that the pressure change is surely detected. In this case, a case where the pressure change is not detected can be prevented to some extent. Contrary, if the pressure change of 0.05 KPa cannot be detected, many cases where the pressure change is not detected are occurred. Further, when the pressure is disposed in a range between 2.5 KPa and 5 Kpa, it is required to detect the pressure change of at least 0.1 KPa so that the pressure change is surely detected. Furthermore, when the pressure is disposed in a range between 5 KPa and 10 Kpa, it is required to detect the pressure change of at least 0.2 KPa so that the pressure change is surely detected.

Here, the sensor 221 having the pressure detection device disposed at the electrode of the membrane switch has a following relationship between the pressure P and the sensor resistance Rs.

$$Rs \cong 10 \times P^{-1} \tag{F1}$$

Further, a resistance ratio (i.e., resistance distribution ratio) of the pressure sensitivity resistance Rv is shown as formula F2.

$$\text{(RESISTANCE RATIO)} = \frac{Rv}{Rv + Rs} = \frac{Rv}{Rv + 10 \times P^{-1}} \quad \text{(F2)}$$

Accordingly, when a certain reference pressure is changed by a pressure change of 0.05 KPa, a difference of the resistance ratio is shown as formula F3.

$$\begin{aligned}\text{(DIFFERENCE OF} \\ \text{RESISTANCE RATIO)}\end{aligned} = \frac{Rv}{Rv + 10 \times P^{-1}} - \frac{Rv}{Rv + 10 \times (P+0.05)^{-1}} \quad \text{(F3)}$$

As shown in FIG. 5, the distribution of the pressure disposed in arrange between 1 KPa and 2.5 KPa is about 60%, the distribution of the pressure disposed in arrange between 2.5 KPa and 5 KPa is about 30%, and the distribution of the pressure disposed in arrange between 5 KPa and 10 KPa is about 10%. Therefore, weightings of each pressure range are six, three and one, respectively. In view of these weightings, an integration Rcal of the difference of the resistance ratio is obtained by formula F4.

$$\begin{aligned}Rcal = &6 \times \int_1^{2.5} \left| \frac{Rv}{Rv + 10 \times P^{-1}} - \frac{Rv}{Rv + 10 \times (P+0.05)^{-1}} \right| dp + \\ &3 \times \int_{2.5}^{5} \left| \frac{Rv}{Rv + 10 \times P^{-1}} - \frac{Rv}{Rv + 10 \times (P+0.1)^{-1}} \right| dp + \\ &\int_5^{10} \left| \frac{Rv}{Rv + 10 \times P^{-1}} - \frac{Rv}{Rv + 10 \times (P+0.2)^{-1}} \right| dp\end{aligned} \quad \text{(F4)}$$

Here, to obtain an optimum sensitivity resistance Rv for providing the maximum difference of the resistance ratio, the sensitivity resistance Rv is determined to maximize the integration Rcal by the above formula F4.

Thus, the optimum sensitivity resistance Rv is obtained. The microcomputer 32 controls the digital potentiometer 231 so that the sensitivity resistance of the digital potentiometer 231 is set to be the optimum sensitivity resistance Rv. In this case, the sensor 221 can detect the pressure change appropriately in a predetermined pressure range, which is a required pressure range.

Figure 6A:
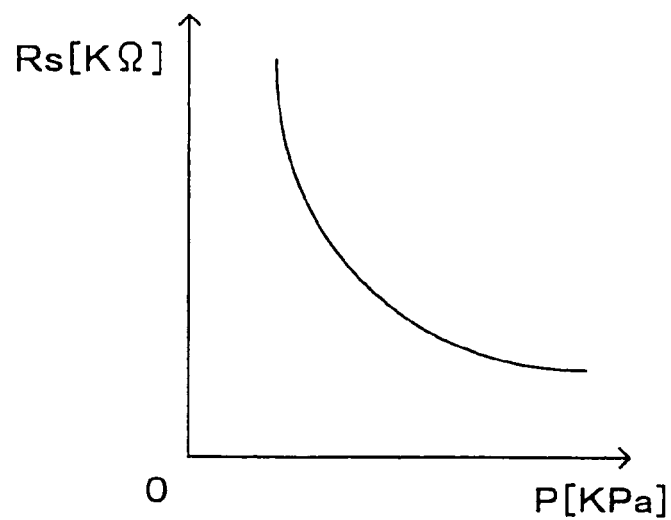
FIG. 6A is a graph showing a relationship between the pressure and a sensor resistance.

Next, the effect of the sensitivity resistance Rv is described as follows. The sensor 221 having the pressure sensitive device disposed at the electrode of the membrane switch has the relationship between the pressure P and the sensor resistance Rs of the sensor 221 shown in formula F1. This relationship is shown in FIG. 6A. The relationship, i.e., the P-Rs characteristic is not a linear dependence with the pressure P. Therefore, if the sensor resistance Rs is determined without using the sensitivity resistance Rv, a waveform in a case where the breath signal is calculated becomes distorted. Accordingly, it is considered that the sensitivity resistance Rv is used in the circuit diagram shown in FIG. 4. In this case, an AD value of the A/D converter 31 is shown as formula F5.

$$\text{(AD VALUE)} = \frac{Rs}{Rv + Rs} \times Vcc \quad \text{(F5)}$$

Figure 6B:
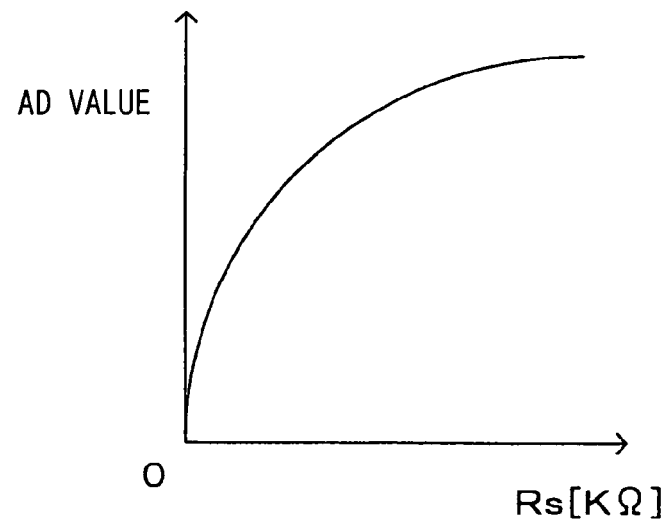
FIG. 6B is a graph showing a relationship between the sensor resistance and an AD value.

The relationship between the AD value and the sensor resistance Rs described in the formula F5 is shown in FIG. 6B. Here, the pressure P in the formula F1 is substituted into the formula so that the sensor resistance Rs is converted to the pressure P. Thus, the following formula F6 is obtained.

$$\text{(AD VALUE)} = \frac{10 \times P^{-1}}{Rv + 10 \times P^{-1}} \times Vcc \quad \text{(F6)}$$

Figure 6C:
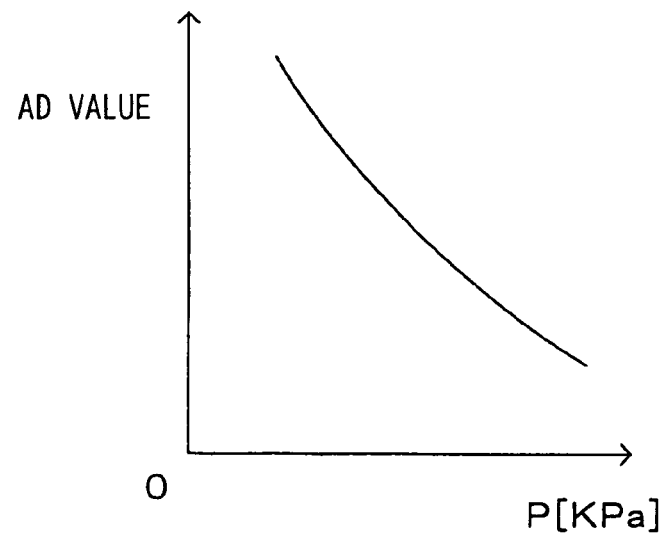
FIG. 6C is a graph showing a relationship between the pressure and the AD value, according to the first embodiment.

The relationship between the AD value and the pressure P described in the formula F6 is shown in FIG. 6C. Thus, the relationship, i.e., the P-AD characteristic is almost a linear dependence with the pressure P, compared with the P-Rs characteristic shown in FIG. 6A. Accordingly, the waveform in a case where the breath signal is calculated does not become distorted substantially.

Figure 7:
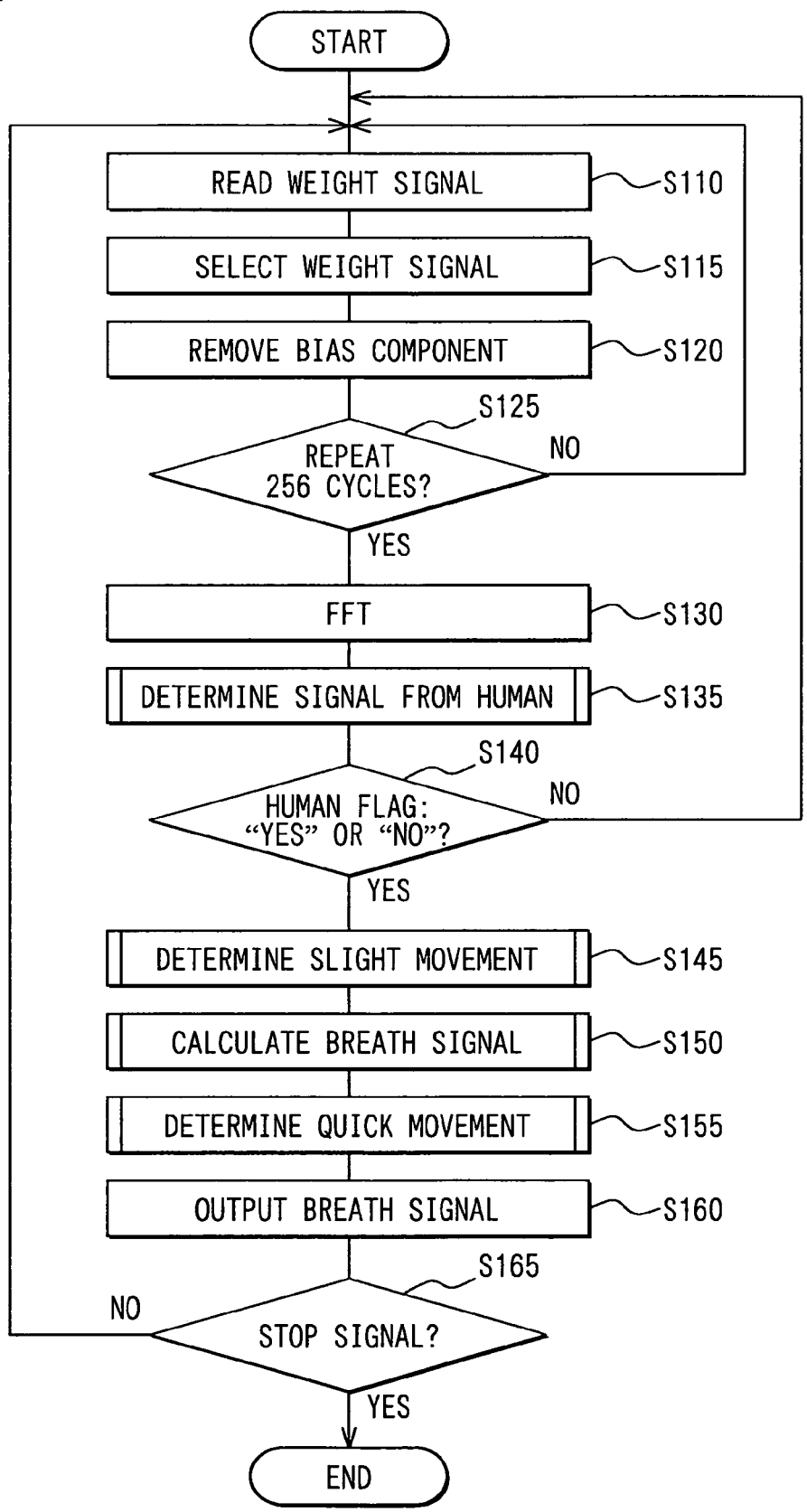
FIG. 7 is a flow chart explaining a breath signal output process, according to the first embodiment.

Next, the breath signal computation process performed by the microcomputer 32 is described with using a flow chart shown in FIG. 7. The breath signal computation process starts to perform a computation when a user (i.e., an operator) operates an operation panel (not shown) of the monitor 50.

At first, the microcomputer 23 starts reading the weight signals in sequence from all of the sensors 221 through the sensor selector 23 and the A/D converter 31 in step S110. Specifically, the microcomputer 23 reads the weight signal of one cycle of each sensor 221. A sampling frequency of the microcomputer 23 is, for example, 10 Hz. Then, the microcomputer 23 selects the weight signals so that each selected weight signal has signal intensity equal to or smaller than a predetermined value (i.e., a threshold) in step S115. Specifically, for example, the microcomputer 23 selects the weight signals having the voltage drop equal to or smaller than a predetermined value. This is because the weight signals only derived from the weight of the bedclothes is removed, and the other weight signals are estimated to derive from the weight of the patient. Here, the weight of the bedclothes is much lighter than the patient so that the weight signal from the bedclothes is larger than that from the weight of the patient. This is, the voltage drop in case of the bedclothes is larger than that in case of the patient. Thus, the microcomputer 23 can select only the weight signals representing the weight of the patient.

Next, a bias component is removed from the weight signals in step S120. Specifically, the weight signals are filtered by a digital filtering method such that a part of the weight signals having a high frequency range equal to or higher than 3 Hz is cut, i.e., removed. Thus, a noise component in the weight signals is removed so that the first signal is provided. The frequency of the first signal is equal to or lower than 3 Hz so that the noise component having a high frequency range higher than a breath frequency of the patient is removed. The breath frequency corresponds to the breath of the patient, and is almost disposed in a range between 0.2 Hz and 0.5 Hz. Then, the first signal is filtered by the digital filtering method such that a part of the first signal having a high frequency range equal to or higher than 0.2 Hz is removed. Thus, a breath component in the first signal is removed so that the second signal is provided. The frequency of the second signal is equal to or lower than 0.2 Hz so that the breath component having the breath frequency is removed. Then, the second signal is subtracted from the first signal so that the weight signal without a bias component is obtained. The weight signal without bias component substantially includes the breath component only. Although the bias component and the noise component are defined to be larger than 3 Hz and to be smaller than 0.2 Hz, these frequencies can be changed. For example, the first signal can be filtered by the digital filtering method such that a part of the first signal having a high frequency range equal to or higher than 0.15 Hz is removed. In this case, the sensor 221 can detect not only a normal breathing but also an irregular breathing having a different frequency different from that of the normal breathing. Here, the normal breathing has a frequency range between 0.2 Hz and 0.5 Hz. In this embodiment, a part of the first signal, which is equal to or higher than 0.3 Hz, is removed.

Next, in step S125, it is decided whether the microcomputer 23 processed the weight signals with two hundred and fifty-six cycles. When the weight signals of 256 cycles are processed, it goes to step S130. When the weight signals of 256 cycles are not processed yet, it goes to step S110. Thus, the microcomputer 23 processes the weight signal of one cycle 256 times repeatedly so that the weight signal having 256 cycles in each sensor 211 are processed. Here, when the sampling frequency is, for example, 10 Hz, a time interval of one cycle is 0.1 seconds. The total time interval of 256 cycles is 25.6 seconds. Therefore, the weight signal outputted from each sensor 221 has the total time interval of 25.6 seconds.

In step S130, the weight signal, which is outputted from each sensor 221, filtered and processed in steps S110-S120, is transformed by a FFT (i.e., fast Fourier transform) method so that a power spectrum of the weight signal is obtained. Specifically, the weight signal outputted from each sensor 221 and including 256 cycles (i.e., having the 25.6 second time interval) is transformed.

Figure 8:
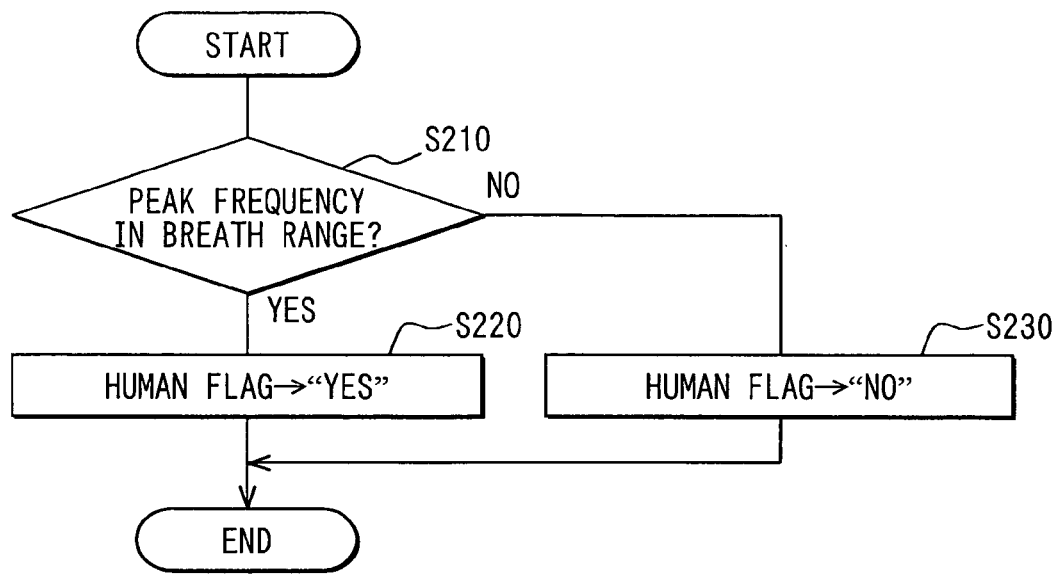
FIG. 8 is a flow chart explaining a human load determination process, according to the first embodiment.

Then, it is determined whether the weight signal is derived from the patient or an object in step S135. Here, this determination process is described in FIG. 8. At first, it is determined whether the power spectrum obtained in step S130 includes a peak in the breath frequency range between 0.2 Hz and 0.5 Hz in step S210. The peak has a peak frequency, i.e., the maximum intensity frequency in the power spectrum. Specifically, it is determined whether the sensor 221 outputs the weight signal composed of 256 cycles having the peak frequency in the breath frequency range. Here, when the power spectrum has multiple peaks, the peak having the maximum intensity is selected so that the frequency of the selected peak is defined as the maximum intensity frequency. Thus, it is decided whether the patient lies on the bed 1, or the object is mounted on the bed 1. Accordingly, even if the object having almost the same weight as the patient is mounted on the bed 1, the monitor can distinguish whether the patient or the object is mounted on the bed 1.

When the sensor 221 includes the weight signal having the peak frequency disposed in the breath frequency range, it goes to step S220, so that a human determination flag (i.e., HUMAN FLAG) is set to be "YES", which means that the patient is mounted on the bed 1. Then, the determination process for determining whether the human or the object is mounted on the bed is ended. Then, it goes to step S135 in the breath signal computation process.

When the sensor 221 does not include the weight signal having the peak frequency disposed in the breath frequency range, it goes to step S230, so that the human determination flag is set to be "NO", which means that no patient is mounted on the bed 1. Then, the determination process for determining whether the human or the object is mounted on the bed is ended. Then, it goes to step S135 in the breath signal computation process.

As shown in FIG. 7, after step S135 is ended, it goes to step S140. It is determined whether the human, i.e., the patient is mounted on the sensor 221, i.e., the bed 1.

Figure 9:
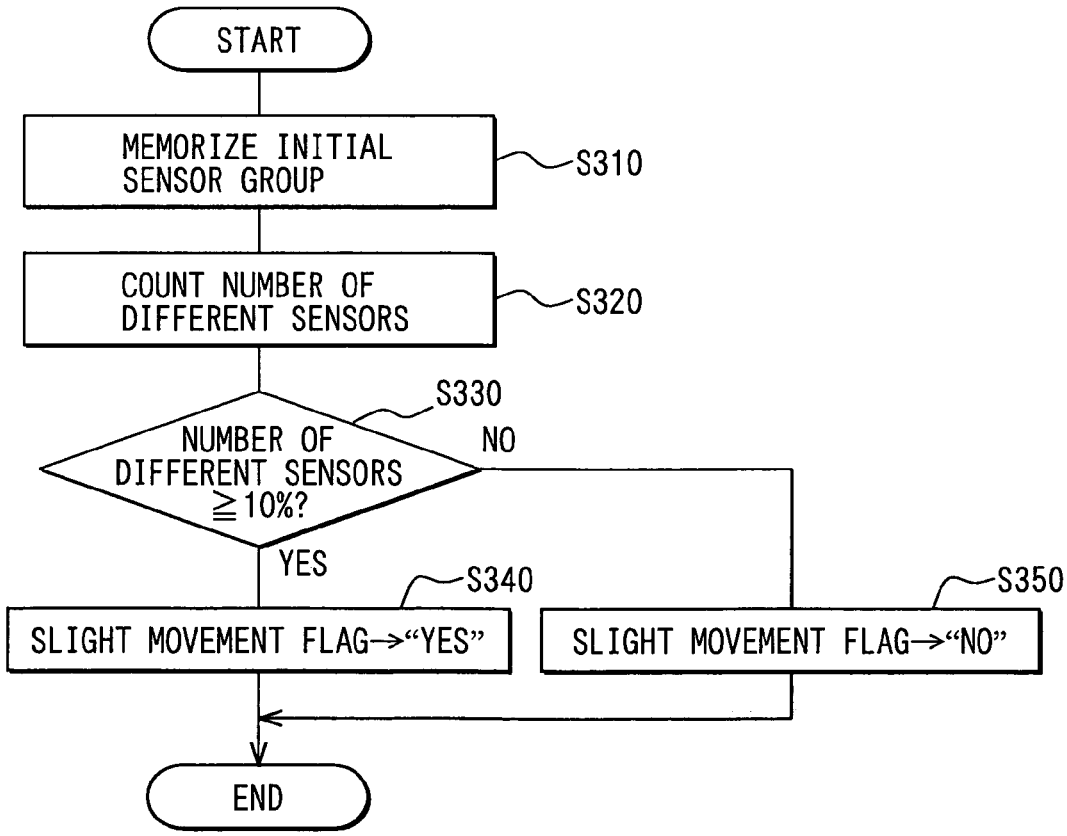
FIG. 9 is a flow chart explaining a slight movement determination process, according to the first embodiment.

Specifically, when the human determination flag is "YES", which means that the human is mounted on the bed 1, it goes to step S145. When the human determination flag is "NO", which means that the human is not mounted on the bed 1, it goes to step S110. In step S145, a slight movement determination process is performed. This slight movement determination process is described in FIG. 9. In step 310, at the first cycle of the 256 cycles of the weight signal, an initial sensor group M(0) is selected. The initial sensor group M(0) is composed of the sensors 221 having the signal intensity equal to or larger than the threshold so that the weight signal is estimated to derive from the weight of the patient. Thus, the initial sensor group M(0) is determined and memorized.

Next, at each cycle in the 256 cycles, each sensor group M(k) (k=1, 2, . . . , 255) composed of the sensors 221 having the signal intensity equal to or larger than the threshold is determined. Then, the sensor group M(k) and the initial sensor group M(0) are compared each other so that the number of the sensors 221 in the sensor group M(k) different from the initial sensor group M(0) is counted in step S320. Thus, the number of the sensors 221 in the group M(k) not being included in the initial sensor group M(0) is counted in each cycle. After the numbers of all of the 255 cycles are decided, it is determined whether one of the numbers of all of the 256 cycles is equal to or larger than 10% of the number of the sensors 221 in the initial sensor group M(k) in step S330. When one of the numbers of the sensors 221 in the sensor groups M(k) different from the sensors 221 in the initial sensor group M(0) is equal to or larger than 10% of the number of the sensors 221 in the initial sensor group M(0), it goes to step S340. When all of the numbers of the sensors 221 in the sensor groups M(k) different from the sensors 221 in the initial sensor group M(0) is smaller than 10% of the number of the sensors 221 in the initial sensor group M(0), it goes to step S350. In step S340, a slight movement flag is set to be "YES", which means that the human moves slightly so that the slight movement is detected by the sensors 221. Then, the slight movement determination process is ended, and then, it goes to step S145 in the breath signal computation process. In step S350, the slight movement flag is set to be "NO", which means that the human does not move slightly so that the human motion is not detected by the sensors 221. Then, the human motion determination process is ended, and then, it goes to step S145 in the breath signal computation process.

Figure 10:
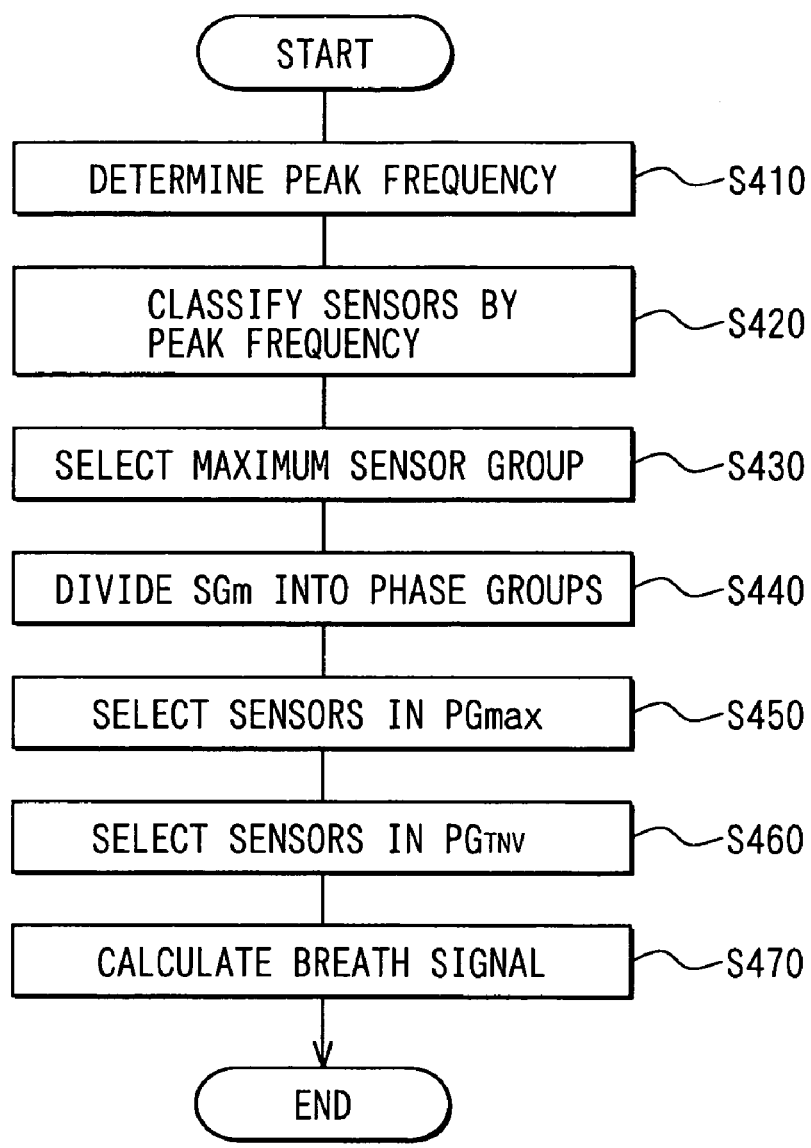
FIG. 10 is a flow chart explaining a breath signal computation process, according to the first embodiment.

After step S145, it goes to step S150. In step S150, a breath signal calculation process is performed. This breath signal calculation process is described in FIG. 10. Firstly, instep S410, the peak frequency obtained from the power spectrum of the weight signal composed of 256 cycles in each sensor 221 is determined in step S410. This power spectrum is obtained instep S130. Thus, each sensor 221 has a different peak frequency. Then, the determined peak frequencies of all sensors 221 are classified into a predetermined frequency range. Then, the number of the sensors 221 having the peak frequency disposed in each frequency range is counted in step S420. Here, for example, the total frequency range between 0.2 Hz and 0.5 Hz is divided into the predetermined frequency ranges having a frequency interval of 0.03 Hz. Thus, the total frequency range is divided at intervals of 0.03 Hz. All of the peak frequencies are classified into the predetermined frequency ranges, respectively. Then, the frequency range having the maximum number of the sensors 221 in the total frequency range is selected so that the sensors 221 composing the maximum number of the sensors 221 disposed in the certain frequency range are classified as a sensor group SGm in step S430. Then, on the basis of the weight signal, i.e., the output signal of each sensor 221 in the sensor group SGm, these sensors 221 in the sensor group SGm are divided into ten phase groups in step S440, each of which has a phase width of π/5. Therefore, ten phase groups are composed of the first phase group PG1 having a phase between 0 and π/5, the second phase group PG2 having a phase between π/5 and 2π/5, . . . , and the tenth phase group PG10 having a phase between 9π/5 and 2π. Then, among ten phase groups PG1-PG10, the maximum phase group PGmax having the maximum number of the sensors 221 is selected instep S450. Thus, the sensors Sm1, Sm2, . . . composing the maximum phase group PGmax are selected. Further, another phase group PGinv having the phase shifted by π from the phase of the maximum phase group PGmax is decided so that the sensors Sn1, Sn2, . . . composing the other phase group PGinv are selected in step S460. Then, the breath signal is calculated according to formula F7 in step S470. Thus, the breath signal calculation process is ended, and then, it goes to step S150 in the breath signal computation process.

$$\text{(BREATH SIGNAL)} = \frac{Sm1 + Sm2 + \cdots + (-1) \times (Sn1 + Sn2 + \cdots)}{N} \quad \text{(F7)}$$

Here, N in the formula F7 represents the number of the sensors Sm1, Sm2, . . . , Sn1, Sn2, . . . obtained by adding the number of the sensors Sm1, Sm2, . . . in the maximum phase group PGmax and the number of the sensors Sn1, Sn2, . . . in the other sensor group PGinv. Further, Sm1, Sn1, and the like in the formula F7 represent the output signals of the sensors Sm1, Sn1, . . . . In this case, the time axis of each output signal of the sensor Sm1, Sn1, . . . is uniformed so that the output signal can be added.

Thus, the breath signal is obtained. Further, the noise derived from the motion of the human is removed as much as possible, and therefore, the breath signal corresponding to the breath of the human can be obtained precisely.

Figure 11:
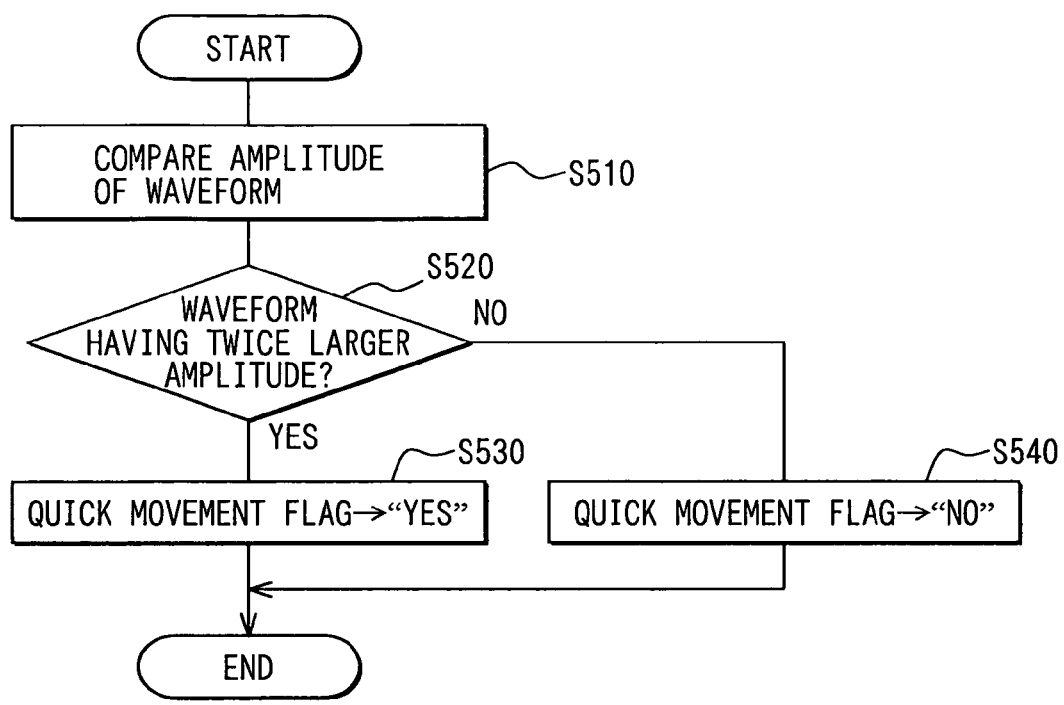
FIG. 11 is a flow chart explaining a quick movement determination process, according to the first embodiment.

After step S150, it goes to step S155. In step S155, a quick movement determination process is performed so that the quick movement is detected when the human moves quickly his four limbs. This quick movement determination process is shown in FIG. 11. Firstly, in step S510, each cycle in the 256 cycles has amplitude of the waveform. The amplitude of one cycle waveform is compared with the amplitudes of the former and latter cycle waveforms. Here, the former cycle waveform and the latter cycle waveform sandwich the one cycle waveform so that the one cycle waveform is disposed between the former and latter cycle waveforms. Then, in step S520, it is determined whether the amplitude of the one cycle waveform is twice larger than the amplitude of the former or later cycle waveform. When the one cycle having the amplitude twice larger than the amplitude of the former or later cycle is disposed in the 256 cycles, it goes to step S530. When no cycle having the amplitude twice larger than the amplitude of the former or later cycle is disposed in the 256 cycles, it goes to step S540.

In step S530, a quick movement flag is set to be "YES", which means that the human moves his limbs quickly. Then, the quick movement determination process for determining whether the human moves his limbs quickly is ended. Then, it goes to step S155 in the breath signal computation process. In step S540, the quick movement flag is set to be "NO", which means that the human does not move his limbs quickly. Then, the quick movement determination process is ended. Then, it goes to step S155 in the breath signal computation process.

After step S155, it goes to step S160. In step S160, the breath signal is outputted to the display 34 so that the display 34 indicates the breath signal as the waveform. Further, the quick movement flag and the slight movement flag are also shown in the display 34. Then, in step S165, it is determined whether a stop signal is inputted into the controller 3. When the stop signal is inputted in the controller 3, the breath signal computation process is ended. When the stop signal is not inputted in the controller 3, it goes to step S110. Thus, the monitor 50 can monitor the breath of the patient by repeating the breath signal computation process. For example, the breath of the patient can be monitored during all night.

According to the above monitor 50, the sensor 221 outputting the breath signal corresponding to the breath of the patient can be selected appropriately so that the breath signal is obtained. Therefore, the accuracy of the breath signal is improved. Further, the monitor 50 can perform the slight movement determination process and the quick movement determination process. Then, the monitor 50 can show the results of the slight movement determination process and the quick movement determination process. Specifically, the display 34 indicates whether the slight movement and/or the quick movement are occurred. Thus, the monitor informs additional information to an observer such as a doctor, a nurse or a technician. Here, the additional information is such that the breath signal may include other signals derived from the quick movement or the slight movement instead of the breath. Thus, the observer for monitoring the breath of the patient can understand the breath signal so that the observer examines, i.e., diagnoses the patient more correctly. Therefore, the monitor can be used for examining a disease such as apnea syndrome.

Although the sensor 221 detects the load, i.e., the pressure, the sensor 221 for detecting a vibration can be used for the monitor 50. For example, a vibration detection sensor detects the vibration of the patient so that the breath signal can be computed from the sensor signal. The vibration detection sensor is, for example, a piezoelectric film device or a PVDF device (i.e., poly vinylidene flouride device).

Second Embodiment

In step S520 in the quick movement determination process shown in FIG. 11, it is determined whether the amplitude of one cycle is twice larger than the amplitude of the former or latter cycle waveform. Further, additional step can be added after step S520. In the additional step, it is determined whether the one cycle having the amplitude twice larger than the amplitude of the former or latter cycle waveform is repeated periodically. When multiple cycles having the amplitude twice larger than the amplitude of the former or latter cycle are disposed in 256 cycles, and the cycles are repeated periodically, the patient may be a periodic leg movement disorder (i.e., PLMD). In this case, the monitor can distinguish the PLMD.

Third Embodiment

The inventors have preliminary studied about detection equipment for detecting apnea state or hypopnea of a human so that a person such as a doctor or a nurse diagnoses apnea syndrome of the human while sleeping. The detection equipment includes a sensor sheet having multiple pressure sensors disposed under the bedclothes, a controller, a display for showing the number of breathing of the patient and/or showing the number of decreasing of oxygen saturation of blood of the patient. Each pressure sensor detects a load, i.e., pressure of the patient and outputs a load signal to the controller so that the controller computes a breath motion signal as a breath signal corresponding to the breathing of the patient. The breath motion signal has a frequency range corresponding to the number of the breathing. When oxygen saturation of blood of the patient is decreased, amplitude of the breath motion signal is changed particularly. Thus, a certain changing pattern of the amplitude of the breath motion signal shows the oxygen saturation of blood according to obstructive apnea. The display shows the number of decreasing of the oxygen saturation of blood. Therefore, the person such as a doctor can diagnose the apnea syndrome on the basis of the information from the detection equipment.

Here, the decrease of the oxygen saturation of blood is determined as follows. For example, when the patient is obstructive apnea syndrome, a muscle of chin is relaxed because of a sleep. Thus, a throat, i.e., an airway is closed or blocked so that oxygen is not supplied to lungs of the patient. Although the patient performs a breathing motion, the oxygen is not supplied to the lungs. Then, the oxygen saturation of blood is decreased. When the oxygen saturation blood is decreased and reaches to a certain low concentration level, the patient temporarily awakes and he breathes deeply. This is, the deep breathing motion is observed. Therefore, the detection equipment determines the decrease of the oxygen saturation of blood on the basis of a sudden increase of the amplitude of the breath motion signal according to the deep breathing.

Here, the apnea syndrome while sleeping includes not only the obstructive apnea and a central apnea but also hypopnea. In the obstructive apnea and the central apnea, the oxygen is not supplied to the lungs completely. In the hypopnea, the airway of the patient is narrowed so that the oxygen is not sufficiently supplied to the lungs. Accordingly, when the patient is the hypopnea, the oxygen supply to the lungs is insufficient. Therefore, the patient having the hypopnea shows similar symptoms to the obstructive apnea. Therefore, the detection equipment for the apnea syndrome is required to detect both of the apnea symptoms and the hypopnea symptoms.

When the detection equipment determines the apnea symptoms on the basis of the sudden increase of the amplitude of the breath motion signal, the detection equipment may not detect the hypopnea symptoms. This is because the amplitude change of the breath motion signal in case of the hypopnea symptoms is comparatively small, compared with the apnea syndrome. Thus, the detection equipment cannot determine the hypopnea symptoms with high accuracy. Further, it is considered that a threshold of the amplitude change to determine the information about the hypopnea on the basis of the amplitude change of the breath motion signal is set to be smaller. However, in this case, the detection equipment may fail to determine the hypopnea. For example, the breath condition change according to the slight body movement may be determined as the hypopnea. Therefore, the detection accuracy of the hypopnea is decreased.

In view of the above problem, detection equipment for detecting both of the hypopnea symptoms and the apnea symptoms is preliminarily provided. This detection equipment determines the hypopnea symptoms and the apnea symptoms on the basis of the frequency change of the breath signal, which is computed from the load signal in accordance with the body movement from the breathing of the patient. This is, a recovery of the breathing motion after the hypopnea symptoms or the apnea symptoms is very quick; and therefore, the quick recovery is detected as a frequency change so that the hypopnea symptoms and the apnea symptoms is determined on the basis of the frequency change.

In this determination method, the hypopnea symptoms and the apnea symptoms are determined on the basis of the breathing after these syndromes. However, when a doctor or the like determines the hypopnea symptoms and the apnea symptoms by diagnosis of the breathing, he takes into account not only the breathing at the hypopnea symptoms and the apnea symptoms but also the breathing before and after the hypopnea symptoms and the apnea symptoms. Thus, the doctor totally diagnoses the breathing during a few minutes so that he determines the hypopnea symptoms and the apnea symptoms. Specifically, the doctor observes one of the hypopnea symptoms or the apnea symptoms, and further, the doctor observes another one of the hypopnea symptoms or the apnea symptoms, which is observed during a few minutes around the one of the hypopnea symptoms or the apnea symptoms. In this case, the doctor diagnoses the hypopnea symptoms or the apnea symptoms. Therefore, in the above method, if the frequency change of the breath signal is caused by a noise instead of the breathing, the detection equipment may fail to determine the breath signal as the hypopnea symptoms or the apnea symptoms.

In view of the above problem, new detection equipment according to a third embodiment of the present invention is provided as follows. A load signal is inputted from the sensor 221 to the controller 3 of detection equipment 51 according to the third embodiment. Thus, the controller 3 computes a breath signal curve on the basis of the load signal in a breath signal computation process. Further, the controller 3 determines the hypopnea symptoms or the apnea symptoms on the basis of the breath signal curve in a determination process so that the controller 3 computes the number of the hypopnea symptoms or the apnea symptoms and the like. Then, the controller 3 controls the display 34 to show the number of the hypopnea symptoms or the apnea symptoms and the like.

Figure 12:
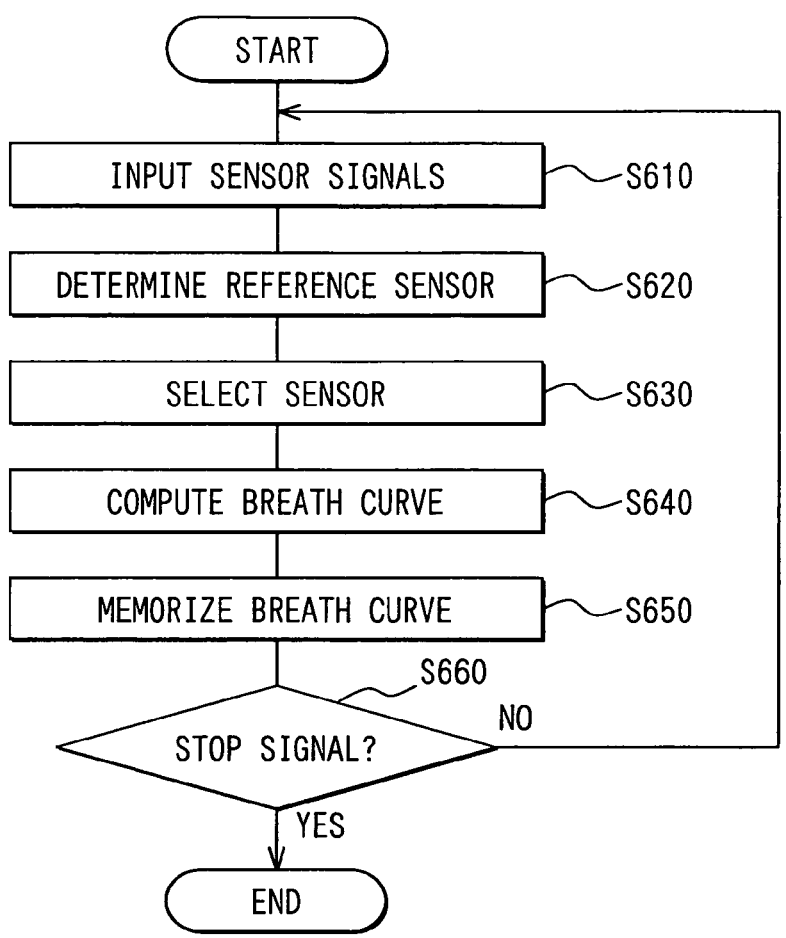
FIG. 12 is a flow chart explaining a breath signal curve computation process, according to a third embodiment of the present invention.

Next, the breath curve computation process performed by the microcomputer 32 of the controller 3 is described. A person as an operator such as a doctor or a nurse operates a panel (not shown), the breath curve computation process is performed. As shown in FIG. 12, firstly, all of the sensor signals generated from the sensor 221 are inputted to the microcomputer 32 through the A/D converter 31 in step S610. Then, in step S620, the sensor signals are filtered by using a band pass filter having a passing frequency range corresponding to the breathing. Then, the filtered sensor signals are transformed by the FFT analysis method so that the power spectrums of the sensor signals are obtained. Each power spectrum has a certain peak having a peak frequency. On the basis of the magnitude of the power spectrum, the sensor 221 detecting the body movement according to the breathing is selected as a reference sensor. Specifically, the sensor 221 outputting the sensor signal having the largest magnitude of the power spectrum disposed in the certain frequency region corresponding to the breathing is selected as the reference sensor for computing the breath signal curve. The sensor 221 having the largest magnitude outputs the sensor signal having the largest change of, load according to the body movement of the breathing. The frequency range is set to be, for example, in a range between 0.15 Hz and 0.55 Hz, which correspond to the number of breathing between 9 times and 33 times per minute. In this case, the sensor 221 can detect not only a normal breathing but also an irregular breathing having a different frequency different from that of the normal breathing. Here, the normal breathing has a frequency range between 0.2 Hz and 0.5 Hz.

Next, in step S630, a cross-correlation function between the reference sensor and each sensor 221 is calculated so that the sensor 221 outputting the sensor signal having substantially the same phase as the reference sensor is determined. Here, the sensor signal having substantially the same phase as the reference sensor is disposed in a range between +⅛ cycle and −⅛ cycle deviated from the center phase of the reference sensor signal outputted from the reference sensor. The range between +⅛ cycle and −⅛ cycle is a range between +π/4 and −π/4. Then, the sensor signal outputted from the selected sensor and the reference sensor signal outputted from the reference sensor are added so that the breath signal curve is computed in step S640. Thus, the breath signal curve corresponding to the breathing can be obtained precisely, since a noise from a body movement except for the breathing is removed.

Here, the sensor 221 outputting the sensor signal having substantially the opposite phase to the reference sensor can be determined. In this case, the sensor signal outputted from the selected sensor is inversed so that the phase of the selected sensor signal is shifted by 180°, and then, the inversed sensor signal and the reference sensor signal outputted from the reference sensor are added so that the breath signal curve is computed. Further, the breath signal curve can be computed such that the inversed sensor signal outputted from the sensor having the opposite phase, the sensor signal outputted from the selected sensor having the same phase, and the reference sensor signal outputted from the reference sensor are added. In this case, assuming that the reference sensor is disposed near a breast of the patient, the selected sensor having the same phase is disposed near the breast, and the sensor having the opposite phase is disposed near a head or an abdomen of the patient.

In step S650, data corresponding to the breath signal curve is memorized in the memory 33. In step S660, when the operator operates the panel so that the breath curve computation process is ended, a stop signal is inputted into the microcomputer 32 so that it goes to end step. However, when the stop signal is not inputted into the microcomputer 32, it goes to step S610 and the breath curve computation process is repeated.

Figure 13:
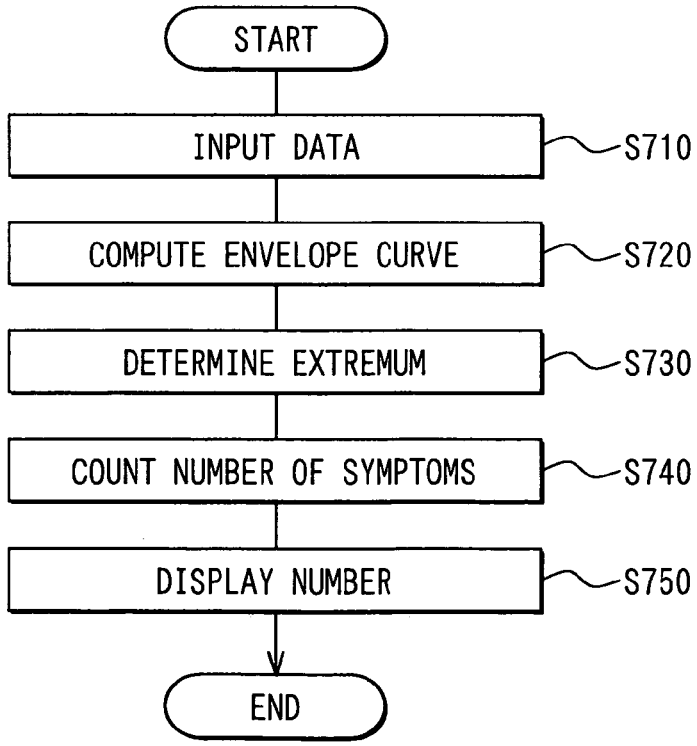
FIG. 13 is a flow chart explaining an apnea symptom diagnosis process, according to the third embodiment.
Figure 14A:
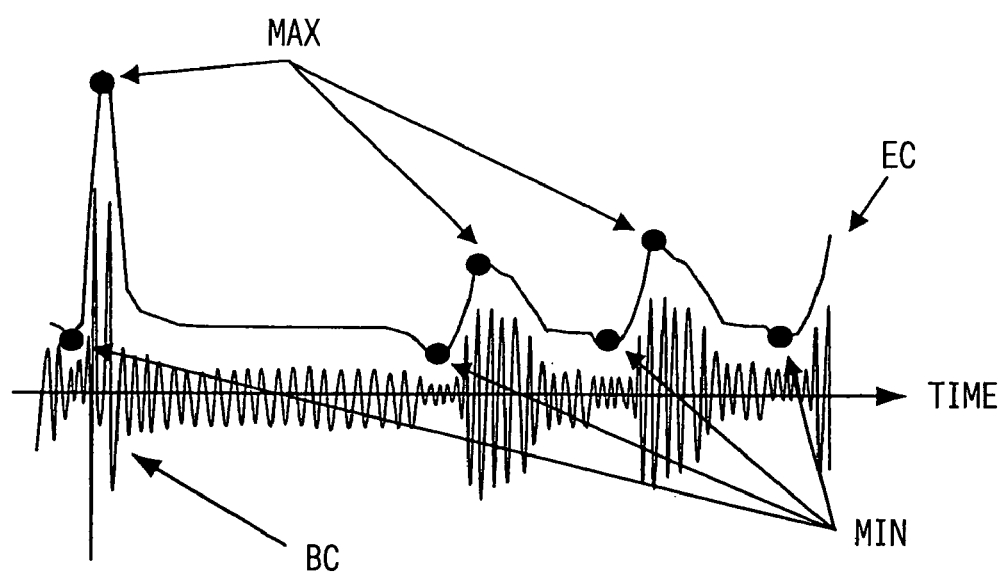
FIG. 14A is a graph explaining an envelope curve.
Figure 14B:
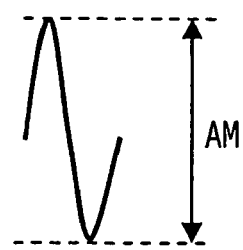
FIG. 14B is a graph showing one cycle of a breath signal curve, according to the third embodiment.

Next, the determination process performed by the microcomputer 32 is described in detail as follows. When the operator operates the panel, the determination process is performed. As shown in FIG. 13, firstly, in step S710, the data of the breath signal curve is inputted from the memory 33 to the microcomputer 32. Then, an envelope curve of amplitude of the breath signal curve is computed on the basis of the inputted data in step S720. The envelope curve EC is shown in FIG. 14A. Here, it is assumed that the breath signal curve BC shown in FIG. 14A is obtained. One cycle of the breath signal curve is picked up, as shown in FIG. 14B. Then, the amplitude AM of the one cycle of the breath signal curve BC is obtained. Thus, all cycles of the breath signal curve BC are processed so that all of the amplitudes AM are obtained. All amplitudes are interpolated so that the envelope curve EC is computed. The envelope curve EC has multiple extremums including maximum values MAX and minimum values MIN. Here, the envelope curve EC can be a discrete curve as long as the extremum is defined substantially.

After the envelope curve EC is computed, it goes to step S730 in FIG. 13. In step S730, the extremums in the envelope curve EC are determined. This determination can be performed by various methods. For example, the envelope curve function is differentiated so that the extremums are determined. Further, since a difference of the amplitude AM is changed from positive to negative or from negative to positive at the extremum, the extremum is determined on the basis of the difference change.

Figure 15:
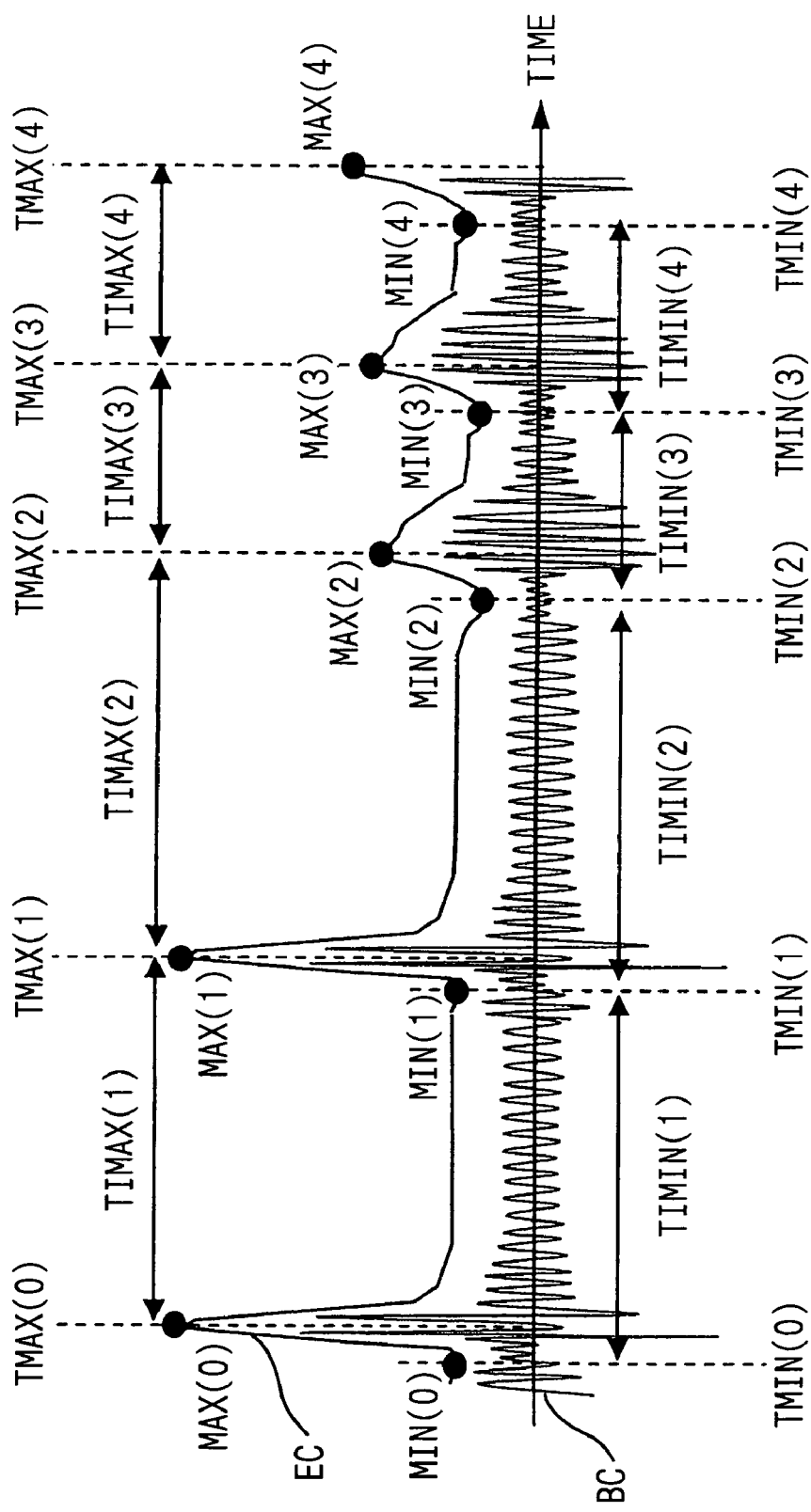
FIG. 15 is a graph explaining periodicity of extremums, according to the third embodiment.

Next, in step S740, the apnea symptom is determined on the basis of periodicity of the extremums so that the number of the apnea symptoms is counted as follows. As shown in FIG. 15, the maximum values MAX(k) (k=0, 1, 2, . . . , N) in the extremums determined in step S730 are appeared at a time TMAX(k) (k=0, 1, 2, . . . , N). The minimum values MIN(k) (k=0, 1, 2, . . . , N) in the extremums determined in step S730 are appeared at a time TMIN(k) (k=0, 1, 2, . . . , N). A time interval TIMAX(k) (k=1, 2, . . . , N) of the maximum values MAX(k) is defined as:

$$TIMAX(k)=TMAX(k)-TMAX(k-1).$$

A time interval TIMIN(k) (k=1, 2, . . . , N) of the minimum values MIN(k) is defined as:

$$TIMIN(k)=TMIN(k)-TMIN(k-1).$$

When the time intervals TIMAX(k), TIMIN(k) of the maximum values MAX(k) and the minimum values MIN(k) satisfy at least one of the following conditions, the apnea symptom is occurred at the time TMIN(k) of the minimum value MIN(k). Thus, the apnea symptom is occurred once at the time TMIN(k). In this way, the number of the apnea symptoms is counted.

First Condition C1:

$$TIMIN(k)<AVMIN+\alpha;\ TIMAX(k)<AVMAX+\alpha;$$

$$TIMIN(k-1)<AVMIN+\alpha;\ \text{and}\ TIMAX(k-1)<AVMAX+\alpha.$$

Second Condition C2:

$$TIMIN(k)<AVMIN+\alpha;\ TIMAX(k)<AVMAX+\alpha;$$

$$TIMIN(k+1)<AVMIN+\alpha;\ \text{and}\ TIMAX(k+1)<AVMAX+\alpha.$$

Third Condition C3:

$$TIMIN(k+1)<AVMIN+\alpha;\ TIMAX(k+1)<AVMAX+\alpha;$$

$$TIMIN(k+2)<AVMIN+\alpha;\ \text{and}\ TIMAX(k+2)<AVMAX+\alpha.$$

In the above conditions, a mean time interval AVMAX of the maximum values MAX(k) is defined as:

$$AVMAX=\Sigma TIMAX(k)/N.$$

Here, N represents the total number of k, i.e., when the integer k represents from 1 to N, the last number of k is defined as N. A mean time interval AVMIN of the minimum values MIN(k) is defined as:

$$AVMIN=\Sigma TIMIN(k)/N.$$

A constant value α represents, for example, 30 seconds, i.e., α=30. Here, the constant value α is determined by an experiment or the like. Therefore, the constant value α is adjusted on the basis of habit of the patient and/or a progression degree of apnea syndrome of the patient. In general, most of the motions not corresponding to the breathing have a large time intervals, compared with that of the motion corresponding to the breathing. Therefore, when the time intervals TIMAX(k), TIMIN(k) of the maximum values MAX(k) and the minimum values MIN(k) are smaller than a predetermined value composed of the mean time interval AVMIN, AVMAX and the constant value α, the detection accuracy of the apnea symptom can be improved.

The above conditions C1-C3 are explained with using FIG. 15. In FIG. 15, for example, the time intervals of the minimum and maximum values are TIMIN(1)=TIMIN(2)= 120 seconds, TIMIN(3)=TIMIN(4)=30 seconds, TIMAX(1)=TIMAX(2)=120 seconds, and TIMAX(3)=TIMAX(4)=30 seconds. In this case, the mean time intervals AVMIN, AVMAX of the minimum and maximum values MIN, MAX are AVMIN=75 seconds, and AVMAX=75 seconds.

Accordingly, when the integer k is 2 (i.e., k=2), the time intervals TIMAX(2), TIMIN(2) satisfy the third condition C3. Further, when the integer k is 3 (i.e., k=3), the time intervals TIMAX(3), TIMIN(3) satisfy the second condition C2. Furthermore, when the integer k is 4 (i.e., k=4), the time intervals TIMAX(4), TIMIN(4) satisfy the first condition C3. However, when the integer k is 1 or 2, (i.e., k=1 or 2), the time intervals TIMAX(k), TIMIN(k) do not satisfy any condition C1-C3. Thus, it is determined that the apnea symptoms are occurred at the times TMIN(2), TMIN(3) and TMIN(4). Accordingly, the number of the apnea symptoms is three.

Next, in step S750 in FIG. 13, the number of the apnea symptoms calculated in step S740 is displayed on the display 34. Thus, the determination process is completed. In the detection equipment according to the third embodiment, the apnea symptom is determined on the basis of the periodicity of the extremums in the envelope curve EC of the breath signal curve BC, the extremums having the possibility of the apnea symptoms. Therefore, the body movement of the patient not corresponding to the breathing, i.e., the body movement not corresponding to the apnea symptoms can be distinguished from the motion according to the breathing, i.e., the apnea symptoms. Here, the body movement of the patient is suddenly happened. However, in general, the apnea symptoms are often happened periodically. Therefore, the body movement according to the apnea symptom having the periodicity is detected precisely. Further, in conventional detection equipment in the prior art, a threshold for preventing a detection error is set in such a manner that an irregular signal such as an irregular amplitude change or an irregular frequency change not derived from ordinal breathing is removed. However, in the detection equipment according to the third embodiment, since the apnea symptom is determined on the basis of the periodicity of the extremums, the threshold can be much reduced when the extremums are determined. Accordingly, the detection equipment can detect a slight apnea symptom, compared with the conventional detection equipment. Here, the periodicity of the extremums implies that the extremums have the periodicity. Further, it implies that the extremums have a periodic characteristic.

Fourth Embodiment

In detection equipment according to a fourth embodiment of the present invention, the apnea symptom is determined when the time intervals TIMAX(k), TIMIN(k) of the maximum and minimum values MAX, MIN satisfy at least one of the following conditions C4-C6. The apnea symptom is occurred at the time TMIN(k) of the minimum value MIN(k). Thus, the number of the apnea symptoms is counted.

Fourth Condition C4:

$AVMIN-\beta<TIMIN(k)<AVMIN+\alpha;$ $AVMAX-\beta<TIMAX(k)<AVMAX+\alpha;$ $AVMIN-\beta<TIMIN(k-1)<AVMIN+\alpha;$ and $AVMAX-\beta<TIMAX(k-1)<AVMAX+\alpha.$ Fifth Condition C5:

$AVMIN-\beta<TIMIN(k)<AVMIN+\alpha;$ $AVMAX-\beta<TIMAX(k)<AVMAX+\alpha;$ $AVMIN-\beta<TIMIN(k+1)<AVMIN+\alpha;$ and $AVMAX-\beta<TIMAX(k+1)<AVMAX+\alpha.$ Sixth Condition C6:

$AVMIN-\beta<TIMIN(k+1)<AVMIN+\alpha;$ $AVMAX-\beta<TIMAX(k+1)<AVMAX+\alpha;$ $AVMIN-\beta<TIMIN(k+2)<AVMIN+\alpha;$ and $AVMAX-\beta<TIMAX(k+2)<AVMAX+\alpha.$ Here, the constant values α, β are determined by an experiment or the like. Therefore, the constant values α, β are adjusted on the basis of habit of the patient and/or a progression degree of apnea syndrome of the patient. For example, the constant value α is 30 seconds, and the constant value β is 50 seconds.

In this case, the body movement of the patient not corresponding to the breathing, e.g., the body movement corresponding to a wiggling motion such as a twitch or a nervous shaking can be distinguished from the motion according to the apnea symptoms. Thus, the detection equipment detects the apnea symptom with high accuracy.

Specifically, when the time intervals TIMAX(k), TIMIN(k) of the maximum and minimum values MAX, MIN are disposed in a certain range shown as the above conditions C4-C6, it is determined that the apnea symptom is occurred at the time TMIN(k). Thus, the time interval TIMIN of the minimum value MIN is disposed in a predetermined range, which is defined on the basis of the mean time interval AVMIN of the minimum value MIN. The time interval TIMAX of the maximum value MAX is disposed in another predetermined range, which is defined on the basis of the mean time interval AVMAX of the maximum value MAX. In general, most of the body movement not corresponding to the breathing has a large time interval, compared with the body movement corresponding to the breathing. Further, the body movement corresponding to a wiggling motion such as a twitch or a nervous shaking has a short time interval, compared with the body movement corresponding to the breathing. Therefore, when the predetermined range and the other predetermined range are defined on the basis of the mean time intervals AVMIN, AVMAX of the minimum and maximum values MIN, MAX, the detection accuracy of the apnea symptom can be improved.

Fifth Embodiment

In detection equipment according to a fifth embodiment of the present invention, the apnea symptom is determined when one of the time intervals TIMAX(k), TIMIN(k) of the maximum and minimum values MAX, MIN satisfies at least one of the following conditions C7-C12. The apnea symptom is occurred at the time TMIN(k) of the minimum value MIN(k). Thus, the number of the apnea symptoms is counted.

Seventh Condition C7:

$$AVMIN-\beta<TIMIN(k)<AVMIN+\alpha; \text{ and}$$

$$AVMIN-\beta21\ TIMIN(k-1)<AVMIN+\alpha.$$

Eighth Condition C8:

$$AVMIN-\beta<TIMIN(k)<AVMIN+\alpha; \text{ and}$$

$$AVMIN-\beta<TIMIN(k+1)<AVMIN+\alpha.$$

Ninth Condition C9:

$$AVMIN-\beta<TIMIN(k+1)<AVMIN+\alpha; \text{ and}$$

$$AVMIN-\beta<TIMIN(k+2)<AVMIN+\alpha.$$

Tenth Condition C10:

$$AVMAX-\beta<TIMAX(k)<AVMAX+\alpha; \text{ and}$$

$$AVMAX-\beta<TIMAX(k-1)<AVMAX+\alpha.$$

Eleventh Condition C11:

$$AVMAX-\beta<TIMAX(k)<AVMAX+\alpha; \text{ and}$$

$$AVMAX-\beta<TIMAX(k+1)<AVMAX+\alpha.$$

Twelfth Condition C12:

$$AVMAX-\beta<TIMAX(k+1)<AVMAX+\alpha; \text{ and}$$

$$AVMAX-\beta<TIMAX(k+2)<AVMAX+\alpha.$$

In this case, the detection accuracy of the apnea symptom is a slight decreased. However, the detection process is simplified so that hard ware and/or a soft ware in the detection equipment are simplified. Thus, the manufacturing cost of the detection equipment is reduced.

Sixth Embodiment

In detection equipment according to a sixth embodiment of the present invention, the apnea symptom is determined on the basis of the periodicity of the extremums in the amplitude envelope curve EC of the breath signal curve BC, which is computed from a difference of time at a peak of the sensor signal. The detection equipment has a determination process similar to the process shown in FIG. 13. Although the envelope curve EC in the process shown in FIG. 13 is computed from the breath signal curve BC in Step S720, the amplitude envelope curve is computed from a frequency curve in the determination process according to the sixth embodiment. The frequency curve is calculated from a difference of time at the peak of the breath signal curve BC. In general, the patient in the apnea symptom breathes with a certain speed of breathing, which is different from that after the patient recovers from the apnea symptom. Accordingly, even when the amplitude envelope curve of the frequency curve is computed from the difference of time, the amplitude envelope curve can be used for determining the apnea symptom.

Such changes and modifications are to be understood as being within the scope of the present invention as defined by the appended claims.

What is claimed is:

1. A breath monitor comprising:

a plurality of sensors for detecting a load derived from a human lying on a bed and for outputting a sensor signal corresponding to the load; and breath signal computation means, wherein the sensors are adapted to be disposed under the human with a predetermined arrangement, wherein the breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors, and wherein the breath signal computation means selects the sensors in such a manner that a peak frequency in the spectrum of each sensor signal is determined, a maximum frequency range having a predetermined frequency width, in which the largest number of peak frequencies of the sensor signals are disposed, is determined, and the sensor signals having the peak frequency disposed in the maximum frequency range are selected.

2. The breath monitor according to claim 1, wherein the sensor is a pressure sensor so that the sensor detects the load derived from a weight of the human.

3. The breath monitor according to claim 1, wherein the sensor is a vibration sensor so that the sensor detects the load derived from a vibration of a body movement of the human.

4. The breath monitor according to claim 1, wherein the breath signal computation means converts the sensor signals by using a fast Fourier transform method.

5. The breath monitor according to claim 1, wherein the spectrum is a power spectrum having a relationship between an intensity and a frequency of the sensor signal.

6. The breath monitor according to claim 1, wherein the spectrum is an amplitude spectrum having a relationship between an amplitude and a frequency of the sensor signal.

7. The breath monitor according to claim 1, wherein the breath signal computation means determines the maximum frequency range by using only the peak frequencies disposed in a predetermined breath frequency range.

8. The breath monitor according to claim 1, wherein the breath signal computation means computes the breath signal in such a manner that the sensor signals outputted from the selected sensors are classified into a plurality of phase groups having a predetermined phase width on the basis of a phase of the sensor signal, a maximum phase group having the largest number of classified sensor signals is determined, an opposite phase group having the phase shifted by a half period from a center phase of the maximum phase group is determined, all phases of the sensor signals disposed in one of the maximum phase group and the opposite phase group are inverted, and the inverted sensor signals in the one of the phase groups are added to the sensor signals in the other one of the phase groups so that the breath signal is obtained.

9. A breath monitor comprising:

a plurality of sensors for detecting a load derived from a human lying on a bed and for outputting a sensor signal corresponding to the load;

breath signal computation means; and determination means for determining a quick movement of the human, wherein the sensors are adapted to be disposed under the human with a predetermined arrangement, wherein the breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors, wherein the breath signal includes a plurality of cycles, the number of which is predetermined, and each of which corresponds to one cycle of breathing of the human, and wherein the determination means arbitrarily selects one cycle of the breath signal, compares an amplitude of the one cycle of the breath signal to an amplitude of another cycle of the breath signal, and determines the quick movement when the amplitude of the one cycle is larger by a predetermined reference value than the amplitude of the other cycle.

10. A breath monitor comprising:

a plurality of sensors for detecting a load derived from a human lying on a bed and for outputting a sensor signal corresponding to the load;

breath signal computation means; and determination means for determining a slight movement of the human, wherein the sensors are adapted to be disposed under the human with a predetermined arrangement, wherein the breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors, wherein the breath signal computation means converts the sensor signals, each of which has a signal intensity larger than a predetermined value so that the sensor signal only derived from the load of the human is selected, wherein the determination means determines the number of the sensor signals having the signal intensity larger than the predetermined value, and wherein the determination means determines the slight movement when the number of the sensor signals changes by a predetermined number as time advances.

11. A breath monitor comprising:

a plurality of sensors for detecting a load derived from a human lying on a bed and for outputting a sensor signal corresponding to the load; and breath signal computation means, wherein the sensors are adapted to be disposed under the human with a predetermined arrangement, wherein the breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors, and wherein the breath signal computation means computes the breath signal by using only the sensor signals having a peak frequency in the spectrum disposed in a breath frequency range.

12. A breath monitor comprising:

a plurality off sensors for detecting a load derived from a human lying on a bed and for outputting a sensor signal corresponding to the load;

breath signal computation means;

a resistance branch circuit having a sensitivity resistor; and a switch for switching a connection between the resistance branch circuit and the sensor, wherein the sensors are adapted to be disposed under the human with a predetermined arrangement, wherein the breath signal computation means converts each sensor signal to a frequency domain so that a spectrum of each sensor signal is obtained, selects the sensors on the basis of the converted sensor signals, and computes a breath signal on the basis of the sensor signals outputted from the selected sensors, and wherein each sensor includes the resistance branch circuit.

13. A breath monitor according to claim 12, further comprising:

sensitivity resistance changing means for changing a resistance of the sensitivity resistor in accordance with a sensor characteristic of each sensor to be connected to the resistance branch circuit.

14. Detection equipment for detecting an apnea syndrome, comprising:

breath signal computation means for computing a breath signal on the basis of a change of a load, which corresponds to a body movement of breathing of a person; and determination means for determining an apnea symptom and a hypopnea symptom of the person on the basis of a periodicity of extremums of an amplitude envelope curve of the breath signal.

15. The detection equipment according to claim 14, wherein the amplitude envelope curve of the breath signal is obtained from a frequency signal calculated from the breath signal.

16. The detection equipment according to claim 14, wherein the amplitude envelope curve includes a plurality of pairs of a maximum value and a minimum value, a pair of which is temporally adjacent each other, and defined as MAX(k) and MIN(k) (k=0, 1, 2, . . . , N), respectively, wherein the maximum value of MAX(k) is occurred at a time defined as TMAX(k) (k=0, 1, 2, . . . , N), wherein the minimum value of MIN(k) is occurred at a time defined as TMIN(k) (k=0, 1, 2, . . . , N), wherein the maximum value of MAX(k) and the temporally adjacent maximum value of MAX(k−1) provide a time interval defined as TIMAX(k)=TMAX(k)−TMAX(k−1), wherein the minimum value of MIN(k) and the temporally adjacent minimum value of MIN(k−1) provide a time interval defined as TIMIN(k)=TMIN(k)−TMIN(k−1), wherein the determination means determines the apnea symptom and the hypopnea symptom occurred at the time of TMIN(k) in a case where the time intervals of TIMIN(k) and TIMAX(k) satisfy a condition of:

$TIMIN(k)<C1;$ $TIMAX(k)<C2;$ $TIMIN(k-1)<C1;$ and $TIMAX(k-1)<C2,$ and wherein C1 and C2 are predetermined constant values.

17. The detection equipment according to claim 16, wherein the time intervals of TIMIN(k) of the minimum values of MIN(k) have an average time interval defined as AVMIN=

$$AVMIN = \sum_{k=1}^{N} TIMIN(k)/N,$$

wherein the time intervals of TIMAX(k) of the maximum values of MAX(k) have an average time interval defined as AVMAX=

$$AVMAX = \sum_{k=1}^{N} TIMAX(k)/N,$$

wherein the predetermined constant values of C1 and C2 are defined as:

C1=AVMIN+α; and

C2=AVMAX+α, and wherein α is a predetermined constant value.

18. The detection equipment according to claim 14,
wherein the amplitude envelope curve includes a plurality of pairs of a maximum value and a minimum value, a pair of which is temporally adjacent each other, and defined as MAX(k) and MIN(k) (k=0, 1, 2, . . . , N), respectively,
wherein the maximum value of MAX(k) is occurred at a time defined as TMAX(k) (k=0, 1, 2, . . . , N),
wherein the minimum value of MIN(k) is occurred at a time defined as TMIN(k) (k=0, 1, 2, . . . , N),
wherein the maximum value of MAX(k) and the temporally adjacent maximum value of MAX(k−1) provide a time interval defined as TIMAX(k)=TMAX(k)−TMAX(k−1),
wherein the minimum value of MIN(k) and the temporally adjacent minimum value of MIN(k−1) provide a time interval defined as TIMIN(k)=TMIN(k)−TMIN(k−1),
wherein the determination means determines the apnea symptom and the hypopnea symptom occurred at the time of TMIN(k) in a case where the time intervals of TIMIN(k) and TIMAX(k) satisfy a condition of:

TIMIN($k$)<C1;

TIMAX($k$)<C2;

TIMIN($k$+1)<C1; and

TIMAX($k$+1)<C2, and wherein C1 and C2 are predetermined constant values.

19. The detection equipment according to claim 18,
wherein the time intervals of TIMIN(k) of the minimum values of MIN(k) have an average time interval defined as AVMIN=

$$AVMIN = \sum_{k=1}^{N} TIMIN(k)/N,$$

wherein the time intervals of TIMAX(k) of the maximum values of MAX(k) have an average time interval defined as AVMAX=

$$AVMAX = \sum_{k=1}^{N} TIMAX(k)/N,$$

wherein the predetermined constant values of C1 and C2 are defined as:

C1=AVMIN+α; and

C2=AVMAX+α, and wherein α is a predetermined constant value.

20. The detection equipment according to claim 14,
wherein the amplitude envelope curve includes a plurality of pairs of a maximum value and a minimum value, a pair of which is temporally adjacent each other, and defined as MAX(k) and MIN(k) (k=0, 1, 2, . . . , N), respectively,
wherein the maximum value of MAX(k) is occurred at a time defined as TMAX(k) (k=0, 1, 2, . . . , N),
wherein the minimum value of MIN(k) is occurred at a time defined as TMIN(k) (k=0, 1, 2, . . . , N),
wherein the maximum value of MAX(k) and the temporally adjacent maximum value of MAX(k−1) provide a time interval defined as TIMAX(k)=TMAX(k)−TMAX(k−1),
wherein the minimum value of MIN(k) and the temporally adjacent minimum value of MIN(k−1) provide a time interval defined as TIMIN(k)=TMIN(k)−TMIN(k−1),
wherein the determination means determines the apnea symptom and the hypopnea symptom occurred at the time of TMIN(k) in a case where the time intervals of TIMIN(k) and TIMAX(k) satisfy a condition of:

TIMIN($k$+1)<C1;

TIMAX($k$+1)<C2;

TIMIN($k$+2)<C1; and

TIMAX($k$+2)<C2, and wherein C1 and C2 are predetermined constant values.

21. The detection equipment according to claim 20,
wherein the time intervals of TIMIN(k) of the minimum values of MIN(k) have an average time interval defined as AVMIN=

$$AVMIN = \sum_{k=1}^{N} TIMIN(k)/N,$$

wherein the time intervals of TIMAX(k) of the maximum values of MAX(k) have an average time interval defined as AVMAX=

$$AVMAX = \sum_{k=1}^{N} TIMAX(k)/N,$$

wherein the predetermined constant values of C1 and C2 are defined as:

$C1 = AVMIN + \alpha$; and $C2 = AVMAX + \alpha$, and wherein α is a predetermined constant value.

22. The detection equipment according to claim 14,
wherein the amplitude envelope curve includes a plurality of pairs of a maximum value and a minimum value, a pair of which is temporally adjacent each other, and defined as MAX(k) and MIN(k) (k=0, 1, 2, . . . , N), respectively,
wherein the maximum value of MAX(k) is occurred at a time defined as TMAX(k) (k=0, 1, 2, . . . , N),
wherein the minimum value of MIN(k) is occurred at a time defined as TMIN(k) (k=0, 1, 2, . . . , N),
wherein the maximum value of MAX(k) and the temporally adjacent maximum value of MAX(k−1) provide a time interval defined as TIMAX(k)=TMAX(k)−TMAX(k−1),
wherein the minimum value of MIN(k) and the temporally adjacent minimum value of MIN(k−1) provide a time interval defined as TIMIN(k)=TMIN(k)−TMIN(k−1),
wherein the determination means determines the apnea symptom and the hypopnea symptom occurred at the time of TMIN(k) in a case where the time intervals of TIMIN(k) and TIMAX(k) satisfy a condition of:

$C3 < TIMIN(k) < C1$;

$C4 < TIMAX(k) < C2$;

$C3 < TIMIN(k-1) < C1$; and $C4 < TIMAX(k-1) < C2$, and wherein C1, C2, C3 and C4 are predetermined constant values.

23. The detection equipment according to claim 22,
wherein the time intervals of TIMIN(k) of the minimum values of MIN(k) has an average time interval defined as AVMIN=

$$AVMIN = \sum_{k=1}^{N} TIMIN(k)/N,$$

wherein the time intervals of TIMAX(k) of the maximum values of MAX(k) has an average time interval defined as AVMAX=

$$AVMAX = \sum_{k=1}^{N} TIMAX(k)/N,$$

wherein the predetermined constant values of C1, C2, C3 and C4 are defined as:

$C1 = AVMIN + \alpha$;

$C2 = AVMAX + \alpha$;

$C3 = AVMIN - \beta$; and $C4 = AVMAX - \beta$, and wherein α and β are predetermined constant values.

24. The detection equipment according to claim 14,
wherein the amplitude envelope curve includes a plurality of pairs of a maximum value and a minimum value, a pair of which is temporally adjacent each other, and defined as MAX(k) and MIN(k) (k=0, 1, 2, . . . , N), respectively,
wherein the maximum value of MAX(k) is occurred at a time defined as TMAX(k) (k=0, 1, 2, . . . , N),
wherein the minimum value of MIN(k) is occurred at a time defined as TMIN(k) (k=0, 1, 2, . . . , N),
wherein the maximum value of MAX(k) and the temporally adjacent maximum value of MAX(k−1) provide a time interval defined as TIMAX(k)=TMAX(k)−TMAX(k−1),
wherein the minimum value of MIN(k) and the temporally adjacent minimum value of MIN(k−1) provide a time interval defined as TIMIN(k)=TMIN(k)−TMIN(k−1),
wherein the determination means determines the apnea symptom and the hypopnea symptom occurred at the time of TMIN(k) in a case where the time intervals of TIMIN(k) and TIMAX(k) satisfy a condition of:

$C3 < TIMIN(k) < C1$;

$C4 < TIMAX(k) < C2$;

$C3 < TIMIN(k+1) < C1$; and $C4 < TIMAX(k+1) < C2$, and wherein C1, C2, C3 and C4 are predetermined constant values.

25. The detection equipment according to claim 24,
wherein the time intervals of TIMIN(k) of the minimum values of MIN(k) has an average time interval defined as AVMIN=

$$AVMIN = \sum_{k=1}^{N} TIMIN(k)/N,$$

wherein the time intervals of TIMAX(k) of the maximum values of MAX(k) has an average time interval defined as AVMAX=

$$AVMAX = \sum_{k=1}^{N} TIMAX(k)/N,$$

wherein the predetermined constant values of C1, C2, C3 and C4 are defined as:

$C1 = AVMIN + \alpha$;

$C2 = AVMAX + \alpha$;

$C3 = AVMIN - \beta$; and $C4 = AVMAX - \beta$, and wherein α and β are predetermined constant values.

26. The detection equipment according to claim 14,
wherein the amplitude envelope curve includes a plurality of pairs of a maximum value and a minimum value, a pair of which is temporally adjacent each other, and defined as MAX(k) and MIN(k) (k=0, 1, 2, ..., N), respectively, wherein the maximum value of MAX(k) is occurred at a time defined as TMAX(k) (k=0, 1, 2, ..., N), wherein the minimum value of MIN(k) is occurred at a time defined as TMIN(k) (k=0, 1, 2, ..., N), wherein the maximum value of MAX(k) and the temporally adjacent maximum value of MAX(k−1) provide a time interval defined as TIMAX(k)=TMAX(k)−TMAX(k−1), wherein the minimum value of MIN(k) and the temporally adjacent minimum value of MIN(k−1) provide a time interval defined as TIMIN(k)=TMIN(k)−TMIN(k−1), wherein the determination means determines the apnea symptom and the hypopnea symptom occurred at the time of TMIN(k) in a case where the time intervals of TIMIN(k) and TIMAX(k) satisfy a condition of:

$C3 < \mathrm{TIMIN}(k+1) < C1;$ $C4 < \mathrm{TIMAX}(k+1) < C2;$ $C3 < \mathrm{TIMIN}(k+2) < C1;$ and $C4 < \mathrm{TIMAX}(k+2) < C2,$ and wherein C1, C2, C3 and C4 are predetermined constant values.

27. The detection equipment according to claim 26, wherein the time intervals of TIMIN(k) of the minimum values of MIN(k) has an average time interval defined as AVMIN=

$$AVMIN = \sum_{k=1}^{N} TIMIN(k)/N,$$

wherein the time intervals of TIMAX(k) of the maximum values of MAX(k) has an average time interval defined as AVMAX=

$$AVMAX = \sum_{k=1}^{N} TIMAX(k)/N,$$

wherein the predetermined constant values of C1, C2, C3 and C4 are defined as:

$C1 = AVMIN + \alpha;$ $C2 = AVMAX + \alpha;$ $C3 = AVMIN - \beta;$ and $C4 = AVMAX - \beta,$ and wherein α and β are predetermined constant values.

28. The detection equipment according to claim 14, further comprising:
a plurality of sensors for detecting a load derived from a human lying on a bed and for outputting a sensor signal corresponding to the load,
wherein the sensors are adapted to be disposed under the human with a predetermined arrangement, and
wherein the breath signal computation means converts each sensor signal to a frequency domain so that a spectrum of each sensor signal is obtained, selects the sensors on the basis of the converted sensor signals, and computes the breath signal on the basis of the sensor signals outputted from the selected sensors.

29. The detection equipment according to claim 28, wherein the spectrum is a power spectrum having a relationship between an intensity and a frequency of the sensor signal.

30. The detection equipment according to claim 28, wherein the breath signal computation means selects the sensors in such a manner that a peak frequency in the spectrum of each sensor signal is determined, a maximum frequency range having a predetermined frequency width, in which the largest number of peak frequencies in the sensor signals are disposed, is determined, and the sensor signal having the peak frequency disposed in the maximum frequency range is selected.

31. The detection equipment according to claim 30, wherein the breath signal computation means computes the breath signal in such a manner that the sensor signals outputted from the selected sensors are classified into a plurality of phase groups having a predetermined phase width on the basis of a phase of the sensor signal, a maximum phase group having the largest number of classified sensor signals is determined, an opposite phase group having the phase shifted by a half period from a center phase of the maximum phase group is determined, all phases of the sensor signals disposed in one of the maximum phase group and the opposite phase group are inverted, and the inverted sensor signals in the one of the phase groups are added to the sensor signals in the other one of the phase groups so that the breath signal is obtained.

32. The detection equipment according to claim 14, wherein the breath signal includes a plurality of cycles, the number of which is predetermined, and each of which corresponds to one cycle of breathing of the person and has an amplitude, and
wherein the amplitude envelope curve is obtained in such a manner that all amplitudes of cycles in the breath signal are interpolated so that the amplitude envelope curve is computed.

33. The detection equipment according to claim 14, wherein the extremums in the amplitude envelope curve are determined in such a manner that an amplitude envelope curve function is differentiated.

34. The detection equipment according to claim 14, wherein the extremums in the amplitude envelope curve are determined in such a manner that a difference of the amplitude is changed from positive to negative or from negative to positive at the extremum.

35. The detection equipment according to claim 14, wherein the amplitude envelope curve includes a plurality of minimum values, which are defined as MIN(k) (k=0, 1, 2, ..., N), wherein the minimum value of MIN(k) is occurred at a time defined as TMIN(k) (k=0, 1, 2, ..., N), wherein the minimum value of MIN(k) and the temporally adjacent minimum value of MIN(k−1) provide a time interval defined as TIMIN(k)=TMIN(k)−TMIN(k−1), wherein the determination means determines the apnea symptom and the hypopnea symptom occurred at the time of TMIN(k) in a case where the time interval of TIMIN(k) satisfies a condition of:

$C3 < TIMIN(k) < C1$; and $C3 < TIMIN(k-1) < C1$, and wherein C1 and C3 are predetermined constant values.

36. The detection equipment according to claim 14, wherein the amplitude envelope curve includes a plurality of minimum values, which are defined as MIN(k) (k=0, 1, 2, ..., N), wherein the minimum value of MIN(k) is occurred at a time defined as TMIN(k) (k=0, 1, 2, ..., N), wherein the minimum value of MIN(k) and the temporally adjacent minimum value of MIN(k−1) provide a time interval defined as TIMIN(k)=TMIN(k)−TMIN(k−1), wherein the determination means determines the apnea symptom and the hypopnea symptom occurred at the time of TMIN(k) in a case where the time interval of TIMIN(k) satisfies a condition of:

$C3 < TIMIN(k) < C1$; and $C3 < TIMIN(k+1) < C1$, and wherein C1 and C3 are predetermined constant values.

37. The detection equipment according to claim 14, wherein the amplitude envelope curve includes a plurality of minimum values, which are defined as MIN(k) (k=0, 1, 2, ..., N), wherein the minimum value of MIN(k) is occurred at a time defined as TMIN(k) (k=0, 1, 2, ..., N), wherein the minimum value of MIN(k) and the temporally adjacent minimum value of MIN(k−1) provide a time interval defined as TIMIN(k)=TMIN(k)−TMIN(k−1), wherein the determination means determines the apnea symptom and the hypopnea symptom occurred at the time of TMIN(k) in a case where the time interval of TIMIN(k) satisfies a condition of:

$C3 < TIMIN(k+1) < C1$; and $C3 < TIMIN(k+2) < C1$, and wherein C1 and C3 are predetermined constant values.

38. The detection equipment according to claim 14, wherein the amplitude envelope curve includes a plurality of pairs of a maximum value and a minimum value, a pair of which is temporally adjacent each other, and defined as MAX(k) and MIN(k) (k=0, 1, 2, ..., N), respectively, wherein the maximum value of MAX(k) is occurred at a time defined as TMAX(k) (k=0, 1, 2, ..., N), wherein the minimum value of MIN(k) is occurred at a time defined as TMIN(k) (k=0, 1, 2, ..., N), wherein the maximum value of MAX(k) and the temporally adjacent maximum value of MAX(k−1) provide a time interval defined as TIMAX(k)=TMAX(k)−TMAX(k−1), wherein the determination means determines the apnea symptom and the hypopnea symptom occurred at the time of TMIN(k) in a case where the time interval of TIMAX(k) satisfies a condition of:

$C4 < TIMAX(k) < C2$; and $C4 < TIMAX(k-1) < C2$, and wherein C2 and C4 are predetermined constant values.

39. The detection equipment according to claim 14, wherein the amplitude envelope curve includes a plurality of pairs of a maximum value and a minimum value, a pair of which is temporally adjacent each other, and defined as MAX(k) and MIN(k) (k=0, 1, 2, ..., N), respectively, wherein the maximum value of MAX(k) is occurred at a time defined as TMAX(k) (k=0, 1, 2, ..., N), wherein the minimum value of MIN(k) is occurred at a time defined as TMIN(k) (k=0, 1, 2, ..., N), wherein the maximum value of MAX(k) and the temporally adjacent maximum value of MAX(k−1) provide a time interval defined as TIMAX(k)=TMAX(k)−TMAX(k−1), wherein the determination means determines the apnea symptom and the hypopnea symptom occurred at the time of TMIN(k) in a case where the time interval of TIMAX(k) satisfies a condition of:

$C4 < TIMAX(k) < C2$; and $C4 < TIMAX(k+1) < C2$, and wherein C2 and C4 are predetermined constant values.

40. The detection equipment according to claim 14, wherein the amplitude envelope curve includes a plurality of pairs of a maximum value and a minimum value, a pair of which is temporally adjacent each other, and defined as MAX(k) and MIN(k) (k=0, 1, 2, ..., N), respectively, wherein the maximum value of MAX(k) is occurred at a time defined as TMAX(k) (k=0, 1, 2, ..., N), wherein the minimum value of MIN(k) is occurred at a time defined as TMIN(k) (k=0, 1, 2, ..., N), wherein the maximum value of MAX(k) and the temporally adjacent maximum value of MAX(k−1) provide a time interval defined as TIMAX(k)=TMAX(k)−TMAX(k−1), wherein the determination means determines the apnea symptom and the hypopnea symptom occurred at the time of TMIN(k) in a case where the time interval of TIMAX(k) satisfies a condition of:

$C4 < TIMAX(k+1) < C2$; and $C4 < TIMAX(k+2) < C2$, and wherein C2 and C4 are predetermined constant values.

* * * * *